United States Patent
Dodds

(10) Patent No.: US 7,865,343 B2
(45) Date of Patent: *Jan. 4, 2011

(54) METHOD OF ANALYZING NUTRITION FOR A CANINE OR FELINE ANIMAL

(76) Inventor: W. Jean Dodds, 938 Stanford St., Santa Monica, CA (US) 90403

( * ) Notice: Subject to any disclaimer, the term of this patent is extended or adjusted under 35 U.S.C. 154(b) by 0 days.

This patent is subject to a terminal disclaimer.

(21) Appl. No.: 12/355,721

(22) Filed: Jan. 16, 2009

(65) Prior Publication Data

US 2009/0132465 A1    May 21, 2009

Related U.S. Application Data

(60) Division of application No. 10/635,707, filed on Aug. 5, 2003, now Pat. No. 7,548,839, which is a continuation-in-part of application No. 09/419,192, filed on Oct. 15, 1999, now Pat. No. 6,730,023, and a continuation-in-part of application No. 09/432,851, filed on Nov. 2, 1999, now Pat. No. 6,287,254.

(60) Provisional application No. 60/403,203, filed on Aug. 12, 2002.

(51) Int. Cl.
*G06G 7/48* (2006.01)
*G01N 33/48* (2006.01)

(52) U.S. Cl. .......................... 703/11; 702/19
(58) Field of Classification Search .................. None
See application file for complete search history.

(56) References Cited

U.S. PATENT DOCUMENTS

| | | |
|---|---|---|
| 3,995,019 A | 11/1976 | Jerome |
| 5,691,157 A | 11/1997 | Gong et al. |
| 5,817,025 A | 10/1998 | Alekseev et al. |
| 5,830,709 A | 11/1998 | Benson et al. |
| 5,911,687 A | 6/1999 | Sato et al. |
| 5,954,640 A | 9/1999 | Szabo |
| 6,018,786 A | 1/2000 | Krick et al. |
| 6,063,028 A | 5/2000 | Luciano |
| 6,081,786 A | 6/2000 | Barry et al. |
| 6,135,055 A | 10/2000 | Pratt |
| 6,136,055 A | 10/2000 | Stanek |
| 6,156,355 A | 12/2000 | Shields, Jr. et al. |
| 6,218,122 B1 | 4/2001 | Friend et al. |
| 6,232,522 B1 | 5/2001 | Harley et al. |
| 6,287,254 B1 | 9/2001 | Dodds |
| 6,358,546 B1 * | 3/2002 | Bebiak et al. ............... 426/232 |
| 6,493,641 B1 * | 12/2002 | Singh et al. .................... 702/32 |
| 6,537,213 B2 | 3/2003 | Dodds |
| 6,730,023 B1 | 5/2004 | Dodds |
| 7,029,441 B2 | 4/2006 | Dodds |
| 7,134,995 B2 | 11/2006 | Dodds |
| 7,296,537 B2 | 11/2007 | Burghardi et al. |
| 2002/0022772 A1 | 2/2002 | Dodds |
| 2003/0135096 A1 | 7/2003 | Dodds |
| 2003/0233984 A1 | 12/2003 | van de Ligt et al. |
| 2005/0090718 A1 | 4/2005 | Dodds |
| 2006/0045909 A1 | 3/2006 | Friesen et al. |
| 2006/0064250 A1 | 3/2006 | Goldstein |
| 2006/0200320 A1 | 9/2006 | Al-Murrani |
| 2007/0118295 A1 | 5/2007 | Al-Murrani |

FOREIGN PATENT DOCUMENTS

| | | | |
|---|---|---|---|
| WO | WO 99-67642 A2 | | 12/1999 |
| WO | WO/2001/028415 | * | 4/2001 |
| WO | WO 01/69487 A1 | | 9/2001 |
| WO | WO 2004/113570 A2 | | 12/2004 |

OTHER PUBLICATIONS

Harrison et al., The Journal of Nutrition, 1987, vol. 117, p. 376-382.*
Dodds (Veterinary Practice, 1992, vol. 4, No. 2, p. 25-31).*
Hetzel et al. (The Journal of Nutrition, 1989, vol. 119: 145-151).*
Williams et al. (Nucleic Acids Research, 1990, vol. 18, No. 22, p. 6531-6535).*
Dodds (Advances in Veterinary Science and Comparative Medicine, 1995, vol. 39, p. 29-95).*
Cunningham (The American Journal of Clinical Nutrition; 1982; 35: 1202-1210).*
Swanson, et al., "Nutritional Genomics: Implication for Companion Animals", The American Society for Nutritional Sciences, (2003) J. Nutr. 133:3033-3040 (18 pages).
Swanson, et al., "Diet Affects Nutrient Digestibility, Hematology, and Serum Chemistry of Senior and Weanling Dogs", Journal of American Science, (2004) J. Anim. Sci. 2004. 82:1713-1724 (19 pages).
Kato, et al., "A Perspective on DNA Microarray Technology in Food and Nutritional Science", Current Opinion in Clinical Nutrition and Metabolic Care, (2005) 8:516-522 (7 pages).
Spielbauer, et al., "Impact of Microarray Technology in Nutrition and Food Research", (2005) Mol. Nutr. Food Res., 49, 908-917 (10 pages).
Swanson, et al., "Canine Nutritional Model: Influence of Age, Diet, and Genetics on Health and Well-Being", Current Nutrition & Food Science, vol. 2, No. 2, May 2006, pp. 115-126(12) (1 page).

(Continued)

*Primary Examiner*—Marjorie Moran
*Assistant Examiner*—Pablo Whaley

(57) ABSTRACT

Selecting the nutrition for an animal or animal group comprises performing a diagnostic test to obtain first data. A data base that comprises first data relating a genomic analysis of a bodily fluid or tissue sample from an animal to a physiological condition and optionally the genotype of the animal is accessed. A data base that comprises second data relating to effects of nutrition on genomic analysis is accessed. The first and second data are processed with input data defining the physiological condition and optionally the genotype of the animal or animal group to derive the nutrition for an animal or animal group.

13 Claims, 18 Drawing Sheets

OTHER PUBLICATIONS

Kristen McNutt, PhD., J.D., The Individualized Prescriptive Foods Era Has Dawned, Nutrition Today, May/Jun. 1993, pp. 43-47, USA.

M.F. Bottcher, M.F. et al., "Total and allergen-specific immunoglobulin A levels in saliva in relation to the development of allergy in infants up to 2 years of age" Clin. Exp. Allergy Sep. 2002, vol. 32, No. 9, pp. 1293-1298.

A.P. Foster et al., "Serum IgE and IgG responses to food antigens in normal and atopic dogs, and dogs with gastrointestinal disease" Vet. Immunol. Immunopathol. May 2003, vol. 92, pp. 113-124.

M.J. Day et al. "The Canine Model of Dietary Hypersensitivity" Proc. Nutr. Soc. Nov. 2005, vol. 64, No. 4, pp. 458-464.

R. Wolter "La nutrition de l'animal de sport" Laboratoire de Nutrition sportive (INRA) Ecole Nationale Veterinaire d'Alfort, Science & Sports 2, (1987) p. 63-93.

E. Wainfan & L. Poirier "Methyl Groups in Carcinogenesis: Effects on DNA Methylation and Gene Expression" Cancer Research (Suppl.,) 52, 2071s-2077s, Apr. 1992.

* cited by examiner

FIG. 9

ANTECH DIAGNOSTICS 17672-A Cowan Avenue Irvine CA 92614 Phone: 800-745-4725

Hemopet  
11330 Markon Drive  
Garden Grove, CA 92841  
Tel: 714-891-2022  
Fax: 714-891-2123

Client # 20073  
Chart #

| Accession No. | Doctor | Owner | Pet Name | Received |
|---|---|---|---|---|
| IRAB34070210 | CASE | BERKSHIRE | GIPPER | 07/07/2002 |
| Species | Breed | Sex | Pet Age | Reported |
| Canine | Golden Retriever | CM | 3Y | 07/08/2002 12:50 PM |

| Test Requested | Results | Reference Range | Units |
|---|---|---|---|
| T3 (RIA) | | | |
| T3 (RIA) | 118 | 45-150 | ng/dL |
| T4 (RIA) | | | |
| T4 (RIA) | 2.58 | 1.0-4.0 | µg/dL |
| FREE T3 | | | |
| Free T3 | 4.2 | 3.0-8.0 | pg/mL |
| FREE T4 (RIA) | | | |
| Free T4 (RIA) | 2.40 | 0.65-3.00 | ng/dL |
| T3 AUTOANTIBODIES | | | |
| T3 Autoantibodies | 1.0 | Less Than 2.0 | |
| T4 AUTOANTIBODIES | | | |
| T4 Autoantibodies | 0.7 | Less Than 2.0 | |
| PARVOVIRUS VACCINE TITER (STANDARD) | | | |
| Parvovirus Vaccine Titer | 1:5 | | TITER |

A titer of 1:5 or greater, with no clinical signs, indicates immunologic response to vaccination. A titer of less than 1:5 indicates poor immunologic response to vaccination.

DISTEMPER VACCINE TITER (STANDARD)  
Distemper, IgG          1:5                                              TITER A titer of 1:5 or greater, with no clinical signs, indicates immunologic response to vaccination. A titer of less than 1:5 indicates poor immunologic response to vaccination.

THYROGLOBULIN AUTOANTIBODIES (Pending)

*FIG. 11*

TEST REQUEST SUBMISSION FORM

W. Jean Dodds, DVM

HEMOPET 11330 Markon Drive, Garden Grove, CA 92841 *Please Note: New Address & Phone Number*

PHONE: 714/ 891-2022    FAX: 714/ 891-2123

(DR. DODDS/HEMOPET: ANTECH ACCT. #20073)

Date: _____

Veterinarian/ Clinic: _____

Address: _____

City: _____ State: _____ Zip: _____

Phone: _____ Fax: _____

Client: _____

Address: _____

City: _____ State: _____ Zip: _____

Phone#/_____ Fax: _____

ANIMAL INFORMATION: Canine *Gold Ret* Feline _____ Equine _____ Other _____

Pet Name: _____ Breed: _____ F ___ M ✓ Altered: Yes ✓ No ___

Date of Birth: 12/28/98    Weight: 78

Brief History & Reason For Test: MAY 9/10  INFLAMMATORY THYROIDITIS
                                        IRAB32024700  5/4/02

(Check test or tests desired and enclose appropriate fees)

| Tests: | Cost: |
|---|---|
| ___ Thyroid Antibody Profile (D8T) Profile (If on therapy, what dose and how many hours post-pill?) | $ 37.50 |
| ___ -- ADD ON TSH to D8T | $ 19.00 |
| ___ -- ADD ON TgAA to D8T | $ 17.00 |
| ___ von Willebrand Test (vWD) | $ 33.00 |
| ___ Profile 6400 (Thyroid & vWD) | $ 56.50 |
| ___ Profile 7200 (CBC, Differential, Superchem & Thyroid Antibody Profile) | $ 59.50 |
| ___ Profile SA150 (7122) Distemper & Parvo Vaccine Titers | $ 28.00 | http://www.itsfortheanimals.com/TSTSUB.HTM

FIG. 13

ANTECH DIAGNOSTICS 17672-A Cowan Avenue Irvine CA 92614 Phone: 800-745-4725

Hemopet  Client # 20073
11330 Markon Drive  *Retest*  Chart #
Garden Grove, CA 92841
Tel: 714-891-2022  IRAB32024700  5 hrs post-pill Thyroxine
Fax: 714-891-2123  5/4/02  0.7 mg BID

| Accession No. | Doctor | Owner | Pet Name | Received |
|---|---|---|---|---|
| IRAB34070210 | CASE | BERKSHIRE | GIPPER | 07/07/2002 |

| Species | Breed | Sex | Pet Age | Reported |
|---|---|---|---|---|
| Canine | Golden Retriever *78 lbs* | CM | 3YRS 7 mo | 07/08/2002 12:50 PM |

| Test Requested | Results | Reference Range | Units |
|---|---|---|---|
| T3 (RIA) | | | |
| T3 (RIA) | 118 | 45-150 | ng/dL |
| T4 (RIA) | | | |
| T4 (RIA) | ↓ 2.58 | 1.0-4.0 | μg/dL |
| FREE T3 | | | |
| Free T3 | 4.2 | 3.0-8.0 | pg/mL |
| FREE T4 (RIA) | | | |
| Free T4 (RIA) | 2.40 | 0.65-3.00 | ng/dL |
| T3 AUTOANTIBODIES | | | |
| T3 Autoantibodies | 1.0 | Less Than 2.0 | |
| T4 AUTOANTIBODIES | | | |
| T4 Autoantibodies | 0.7 | Less Than 2.0 | |
| PARVOVIRUS VACCINE TITER (STANDARD) | | | |
| Parvovirus Vaccine Titer | 1:5 | *Adequate Level* | TITER |

A titer of 1:5 or greater, with no clinical signs, indicates immunologic response to vaccination. A titer of less than 1:5 indicates poor immunologic response to vaccination.

DISTEMPER VACCINE TITER (STANDARD)
Distemper, IgG  1:5  TITER

A titer of 1:5 or greater, with no clinical signs, indicates immunologic response to vaccination. A titer of less than 1:5 indicates poor immunologic response to vaccination.

→ THYROGLOBULIN AUTOANTIBODIES (Pending)  *7/8/02*

*Dear Colleague: T4 looks low here but rest is adequate.*

| Adult Optimal Levels | T4 3-5 μg/dl | FT4 1-3 ng/dl | T4AA < 2.0 | *2* |
| | T3 50-150 ng/dl | FT3 3-8 pg/ml | T3AA < 2.0 | |

X  Optimal therapeutic response levels should be in the upper 1/3 to 25% above the upper limits of the resting optimal ranges at 4-6 hours post-BID thyroid medication.
*unless TgAA remains as high as 5/4/02*
X  Thyroid levels are fine at the current dose. Recommend annual retesting.  *(>4000!)*

☐  Thyroid levels are too high. Recommend reducing current dosage of thyroid supplement by _____ (e.g. _____ mg BID), and retest after another 4-6 weeks.

*FIG. 14A*

| Accession No. | Doctor | Owner | Pet Name | |
|---|---|---|---|---|
| IRAB34070210 | CASE | BERKSHIRE | GIPPER | |
| Test Requested | Results | | Reference Range | Units |

☐ Thyroid levels are too low. Recommend increasing current dosage of thyroid supplement by _____ (e.g. _____ mg BID), and retest after another 4-6 weeks.

*[signature]*

Vaccine Titer Serology

X   Serologic/vaccine titers for distemper and parvovirus show <u>adequate humoral immunity</u> indicating that this dog should respond with a boosted anamnestic response to afford protection against these agents upon exposure.

X   Recheck serologic/vaccine titers annually.

*[signature]*

FIG. 14B

| | | | |
|---|---|---|---|
| Adult Optimal Levels | T4 2-4 µg/dl | FT4 1-3 ng/dl | T4AA < 2.0 |
| | T3 50-150 ng/dl | FT3 3-8 pg/ml | T3AA < 2.0 |

☐ Thyroid levels are adequate, borderline normal, very good, or excellent.

☐ Recommend annual retesting during anestrus.

☐ Thyroid results are borderline normal. Recommend retesting in _____ months.

*W. Jean Dodds, DVM*

| | | | |
|---|---|---|---|
| Adult Optimal Levels | T4 2-4 µg/dl | FT4 1-3 ng/dl | T4AA < 2.0 |
| | T3 50-150 ng/dl | FT3 3-8 pg/ml | T3AA < 2.0 |

☐ Thyroid levels are below minimal expectations for a healthy performance adult (at least 1.5 µg/dl for T4 and 1.0 ng/dl for FT4).

☐ Thyroid levels are too low. Recommend 6-8 weeks of Soloxine® or equivalent product at 0.1mg per _____lbs twice daily (e.g._____mg BID) is recommended, followed by retesting thyroid profile 4-6 hours post-pill to monitor response levels.

☐ If clinical signs support thyroid dysfunction, a 6-8 week trial of Soloxine® or equivalent product at 0.1mg per _____ lbs twice daily (e.g. _____ mg BID) is recommended, followed by retesting thyroid profile 4-6 hours post-pill to monitor response levels.

☐ Optimal therapeutic response levels should be in the upper 1/3 to 25% above the upper limits of the resting optimal ranges at 4-6 hours post-BID thyroid medication.

*W. Jean Dodds, DVM*

| | | | |
|---|---|---|---|
| Adult Optimal Levels | T4 2-4 µg/dl | FT4 1-3 ng/dl | T4AA < 2.0 |
| | T3 50-150 ng/dl | FT3 3-8 pg/ml | T3AA < 2.0 |

☐ These results confirm autoimmune thyroiditis, the heritable form of canine thyroid disease. Elevated levels of T3AA and/or T4AA cause <u>spurious</u> elevations in T3/FT3 and/or T4/FT4 because these circulating autoantibodies interfere with laboratory tests of thyroid analytes. The lymphocytic infiltration and gradual destruction of thyroid tissue progresses to end-stage hypothyroidism, as determined by the clinical signs and low T4 and/or FT4 values referable to

*FIG. 15A* thyroid disease. Recommend 6-12 weeks of Soloxine ® or equivalent product at 0.1 mg per _____ lbs twice daily (e.g. _____ mg BID). Retest thyroid profile drawing the sample 4-6 hours post-pill (to reassess levels which should be upper 1/3 to 25% above the resting ranges, and see if thyroid AA levels are waning).

☐ Elevated levels of thyroglobulin autoantibodies are diagnostic of lymphocytic thyroiditis.

☐ As autoimmune thyroiditis is the heritable form of canine thyroid disease, we do NOT recommend using this dog for breeding.

Von Willebrand Disease

☐ vWF: Ag level is normal.

☐ vWF: Ag level is probably normal. You may elect to retest this dog at some later date to confirm status.

☐ vWF:Ag level is borderline normal (equivocal) indicating that the dog may be a carrier of von Willebrand disease (vWD). What do we know about the vWD status of the parents? Recommend retesting or breeding this dog only to mates with normal vWF:Ag levels (>70%), and checking their pups.

☐ vWF:Ag level is abnormal indicating that the dog is a carrier of vWD. What do we know about the vWD status of the parents? Recommend breeding only to mates with normal vWF:Ag levels of (>70%), and checking their pups.

☐ vWF:Ag level is low and this patient has clinical signs of a bleeding tendency, indicating presence of vWD (affected animal). We do not recommend using the animal for breeding. Please contact us if we can help with advice and/or blood products to treat the dog (HEMOPET blood bank # 949-252-8455).

Vaccine Titer Serology

☐ Serologic/vaccine titers for distemper and parvovirus show <u>adequate humoral immunity</u> indicating that this dog should respond with a boosted anamnestic response to afford protection against these agents upon exposure.

☐ Recheck serologic/vaccine titers annually.

FIG. 15B

☐ Serologic/vaccine titers show humoral immunity for distemper and parvovirus of <u>less than optimal</u> levels. This <u>may</u> mean that the dog is less than adequately protected against these agents in the event of exposure.

☐ Recommend booster vaccination for distemper and parvovirus. Recheck titers again after at least 3 weeks or assume that humoral immunity has been boosted appropriately.

☐ Consider booster vaccination for distemper and parvovirus unless the dog has history of adverse vaccine reaction, immune-mediated disease, or some other immune dysfunction.

☐ Minimize risk for exposure to infectious diseases by avoiding areas where many animal congregate or exercise etc.

FIG. 15C

METHOD OF ANALYZING NUTRITION FOR A CANINE OR FELINE ANIMAL

RELATED APPLICATION

This application is a divisional of application Ser. No. 10/635,707, filed Aug. 5, 2003, now issued U.S. Pat. No. 7,548,839, which is a continuation-in-part of and relates to application Ser. No. 09/419,192, filed Oct. 15, 1999, now issued U.S. Pat. No. 6,730,023, and also application Ser. No. 09/432,851 filed Nov. 2, 1999 now issued U.S. Pat. No. 6,287,254. This Application also relates to Provisional Application No. 60/403,203, filed Aug. 12, 2002. The contents of all those applications are incorporated by reference herein.

BACKGROUND

1. Field

This disclosure is concerned with animal health diagnosis. More particularly, the disclosure is directed to the testing, diagnosis and prediction of diseases and disorders of animal companions, for instance dogs and cats.

Further this disclosure relates to a method, system and apparatus for the management of comprehensive and cumulative genetic and health assessment databases in relation to animals worldwide. In particular, the disclosure relates to a bioinformatics system and its implementation in relation to animal biological data.

More specifically the disclosure is directed to animal health care, well-being and nutrition, and methods and systems for enhanced determination of these factors.

2. General Background

There is a need for a new database management bioinformatics scheme and relational database, together with computerized networks that manage, analyze, and/or integrate comprehensive and cumulative animal health assessment data and genetic identifier, genomic mapping, and genetic assessment data. A comprehensive approach to animal health and genetic selection or management of animals, and their clinical care is the subject of the present disclosure.

Current laboratory and research systems and computerization have not achieved this, nor have communication protocols been used effectively in this technological area to facilitate such a relationship or relational bioinformatics database system for management and dissemination of this comprehensive and cumulative information.

More specifically, it is necessary in animal health diagnosis and care that appropriate predictive testing for diseases and disorders of animals be achieved in order to reduce morbidity and mortality, and improve the quality of life and lifespan. Currently this is not done in relation to the health assessment data of an animal together with the genetic data related to that same animal. Current tests do not provide as much data as possible to attain correct diagnosis and disorder predictions with the net result of an improvement in the quality of life and increased longevity.

More so, currently available testing is unnecessarily complex and expensive in relation to the ability to be an accurate predictor of diseases and disorders in animals, and hence their likely longevity.

Additionally there is a difficulty of easily obtaining, reading, diagnosing and reporting to clients the diagnosis in a fast and effective means. Many systems are too complicated and have been premised on the basis of total automation. There is a need for permitting the effective human interaction in computerized data for achieving effective diagnosis, and reporting of that diagnosis in a user-friendly manner.

SUMMARY

The disclosure is directed to a method, apparatus and system of obtaining, analyzing and reporting laboratory test data in relation to the health assessment data of an animal together with the genetic data related to that same animal.

The disclosure also provides a bioinformatics system for inputting, controlling, analyzing and outputting of a broad range of criteria related to the health, genetic background and longevity of animals. This includes a system concerning phenotype data and genetic data relating to animals. Further, there is provided a system for screening of genetic data and genomic mapping, and integrating the phenotype health assessment data and genetic identifier and assessment data in a computerized data processing resource ("CDPR"). Moreover, there is provided a system for analyzing the health assessment or phenotypic data with the interrelated genetic or genotypic data. Thereafter, those data and analyses are communicated from the CDPR in a broad range and in a manner that has not previously been possible.

The present disclosure offers a unique solution to above-described problems by providing an apparatus, method and system, in relation to animals, for performing data analyses of biological specimens from specific subject animals or animal groups in relation to specific subject animal or animal groups of genetic data. The apparatus, method and system comprises a controller for obtaining, inputting, and analyzing biological, physiological, and pathological test data together with genomic mapping and genetic screening data into the CDPR.

The biological, physiological, and pathological data of the subject animal or animal group and the genetic data of the subject animal or animal group are communicated to a remote user as raw data or as related, analyzed biological, physiological, and pathological data and genetic data. The remote user can also appropriately access the CDPR to input data to, or obtain data from, the CDPR.

According to a further aspect of the disclosure there is a dynamic method and system of managing the health care and well-being of a non-livestock pet animal subject.

A computer is at least one of an expert system or interrelationship program or network for determining data base and data relationships. This can be a system such as a neural network, or other statistical sampling systems and networks.

The disclosure also includes the step of reporting the determination of the health care, well-being, nutrition or other therapeutic requirements and suggestions or health on a communications network including the Internet. Preferably, there is a payment procedure for the report which is achieved through the Internet. This communication network and structure is described here in further detail.

There is provided means for inputting data into databases, storing the data in these databases, analyzing the data in a relational sense from the different databases, and retrieving the data from these databases, namely the databases which are part of the CDPR.

A further aspect of the disclosure is the accessibility of the health assessment database and/or genetic database or other databases of the CDPR by the remote user selected on the basis of password, security control, and financial payment such that the data can be transmitted into and from the CDPR by a computer network. Use of selected passwords, encryption systems, and payment systems are employed to facilitate and restrict the flow of data in and/or out of the databases.

Alerts can be set up to advise of attempts at unauthorized access to the CDPR. The computer network may conveniently include the Internet.

As required, the data in the CDPR can also be distributed to multiple authorized remote parties, namely third parties for research or other analysis. The disclosure also includes a method and system for achieving this.

A diagnosis of the health of an animal is obtained through a combination of computerized data analysis, and human interpretation. Data relates to the physical characteristics of the animal, and includes data obtained from a physical inspection of the animal. A blood or other fluid sample is used to obtain a computer generated laboratory analysis. This is reported through an internet network to specialist for analysis by a specialist clinical pathologist. The clinical pathologist has the data relating to the physical characteristics, and thereby makes a diagnosis of the animal's overall health status.

A drop-down menu on a computer screen provides supplemental reports to support the diagnosis. This supplemental report can be generated electronically as determined by criteria pre-selected by a specialist which matches the analysis and the data relating to the physical characteristics This can be enhanced by further input from the specialist pathologist through an entry, selectively a keyboard entry, into the computer to obtain an integrated computer report having the laboratory analysis, supplemental report, and selectively, an enhanced report. Oral input to a computer through voice recognition software may be effective in developing the enhanced report. The integrated or enhanced report is electronically or otherwise communicated to a remotely located client.

In one preferred form of the disclosure, the laboratory analytical report is reported in a first computer program and the drop down-menu is in a second computer program. The data from the first computer program is transferred to the second computer program.

The electronic communication to the client is selectively by e-mail or fax, and the second computer program includes a utility to transmit the integrated report from the second program through the utility.

In the system using a drop-own menu, the drop-down menu is contained in a tool bar supplementing an application, selectively a word processing program. Computer program applications other than word processing applications may be the basis for the supplemental report. The tool bar includes icons defining predetermined supplemental report characteristics, and selected icons may be used by the clinical pathologist to supplement the laboratory analytical report. The icons can be grouped for animal characteristics dependant on age and sex. Alternatively or additionally, the icons are grouped for animal characteristics dependant upon animal grouping. Alternatively or additionally, the icons are grouped for selected disease states, examples of the states being selectively thyroid disease, behavior, autoimmune disease, and cancer. The icons also can be grouped for selected levels of immunity from infectious disease, that being the titer of immunity from the disease causing agent (s) in the animal, and therefore the need for vaccination of the animal against the disease.

The menu, represented by the icons, which define predetermined supplemental report characteristics, are selected to be used by the clinical pathologist to supplement the laboratory analytical report, whether the supplemental report is generated automatically by computer or by manual input from the specialist. The menu can be grouped for animal characteristics dependant on age and sex. Alternatively or additionally, the menu is grouped for animal characteristics dependant on animal grouping. Alternatively or additionally, the menu is grouped for selected disease states, examples of the states being selectively thyroid disease, behavior, autoimmune disease, and cancer. The menu also can be grouped for selected levels of immunity from infectious disease, that being the titer of immunity from the disease agent(s) in the animal, and therefore the need for vaccination of the animal against the disease.

The data includes a panel of tests related to at least one of endocrine function, immunologic function, gastrointestinal function and nutritional analysis, inborn errors of metabolism, paternity, DNA fingerprinting, hemostasis and coagulation function, vaccinal antibody status, adverse and potential adverse vaccine reaction, infectious diseases, pathology, blood typing and bone marrow analysis, cell cytotoxicity, cytokine and allergy testing, and markers of neoplastic and paraneoplastic change. These data are relevant to the likely morbidity, likely longevity, and/or the potential risk for disease or disorder for the animal.

A method and system of obtaining and electronically delivering an assessment of the thyroid function of an animal is achieved through a combination of computerized data and human interpretation related to the animal. Data relating to the physical characteristics of the animal is obtained, the data being from at least one of a physical inspection of the animal, family and breed history, and the data submitted to a clinical pathologist. A blood or other body fluid sample from the animal is submitted for laboratory analysis of the total T4, total T3, free T4, free T3, T3 autoantibody, T4 autoantibody and thyroglobulin autoantibody. Endogenous TSH also can be measured.

A computer generated report of the laboratory analysis is obtained, and reported through a network, selectively an internet network, to a clinical pathologist. The clinical pathologist has the data relating to the physical, and family and breed history characteristics, and makes a first assessment off the thyroid function of the animal. From a drop-down menu on a computer screen a supplemental report to support the assessment is generated. This can be selectively enhanced by a further input from the pathologist through data, through entry, selectively keyboard entry, into the computer. The assessment is dependant on animal grouping and/or on animal age and sex.

An integrated computer report having the laboratory analysis, supplemental report, and an selectively enhanced report is communicated to a remotely located client, such communicating being electronic.

According to a further aspect of the disclosure, data includes characteristics related to autoimmune thyroiditis of the animal. Biological laboratory test data from a bodily fluid or tissue of an animal are analyzed. The test data relate to a physiologic or genetic marker for autoimmune thyroiditis of the animal. The data relates to at least one of the results of a comprehensive thyroid autoantibody test profile, DNA fingerprint (the gene map), and markers for immunoglobulin receptors on B-cells, T-cell receptors, and protein products of the major histocompatibility complex (MHC) genes (Class I and II allellic HLA, DLA or equivalent antigenic specificities) of the animal. Example assays to screen for MHC genes include restriction fragment length polymorphism (RFLP), polymerase chain reaction (PCR) RFLP, PCR sequence-specific oligonucleotides (SSO) and PCR sequence-specific primers (SSP). The values should fall within predetermined levels as a determinant of autoimmune thyroiditis.

According to a further aspect of the disclosure, the data includes characteristics related to the tissue environment of the eye and brain (ocular and blood-brain barrier) which are sites protected from the normal immunologic surveillance mechanisms. Biological laboratory test data from a bodily fluid or tissue of an animal are analyzed. The test data relate to the soluble and cellular immune inflammatory response mediators (cytokine and chemokine levels, immunoglobulin levels, and lymphycyte susbset markers). The value should fall within predetermined levels as a determinant of integrity of protected immune surveillance mechanisms.

According to a further aspect of the disclosure, the data includes characteristics related to the tendency to bleed excessively are determined. Biological laboratory test data from a bodily fluid or tissue of an animal are analyzed. The test data relate to a comprehensive assessment of the hemostatic and coagulation function. The value should fall within predetermined levels as a determinant of the presence of bleeding disorder.

According to another aspect of the disclosure there is provided a method and system of obtaining and electronically delivering an assessment of the thyroid function of an animal through a combination of computerized data and human interpretation related to the animal. Data is obtained relating to the physical, and family and breed history characteristics of the animal, the data being obtained from at least one of a physical inspection and family and breed history of the animal, or other analysis of the animal. The data is submitted to a clinical pathologist.

A blood or other bodily fluid sample is secured from the animal and is submitted for laboratory analysis of the total T4, total T3, free T4, free T3, T3 autoantibody, T4 autoantibody and thyroglobulin autoantibody. Endogenous TSH also can be measured. A computer generated report of the laboratory analysis; is obtained. The report is related to a selected supplemental database for supplemental analysis, and the supplemental analysis is related to the data relating to the physical characteristics, and family and breed history. A first assessment of the thyroid function of the animal is possible.

The supplemental report is selectively enhanced by a further input from a pathologist through data, through entry, selectively keyboard entry, into the computer. An integrated computer report having the laboratory analysis, supplemental report, and selectively an enhanced report is obtained. This is communicated as the integrated or enhanced report to a remotely located client, such communicating being electronic.

Further aspects of the present disclosure will become apparent in the course of the following description and by reference to the attached drawings.

BRIEF DESCRIPTION OF THE DRAWINGS

FIG. 9 is an expanded more detailed report of some of the test data of the patient shown in FIG. 8.

FIG. 11 is a print out of the test data report as shown in FIG. 10.

FIG. 13 is a representative test request submission form relating to the patient, the submission form containing further data and information about the patient.

FIGS. 14A and 14B are representations of the test data report of FIG. 11 having super-imposed additional data inserted through the use of selected icons on the tool bar of FIG. 12, and having added manually written comments.

FIGS. 15A to 15C represent different diagnostic comments represented by the use of different icons from the toolbar.

DETAILED DESCRIPTION OF THE PREFERRED EMBODIMENT

Figure 1:
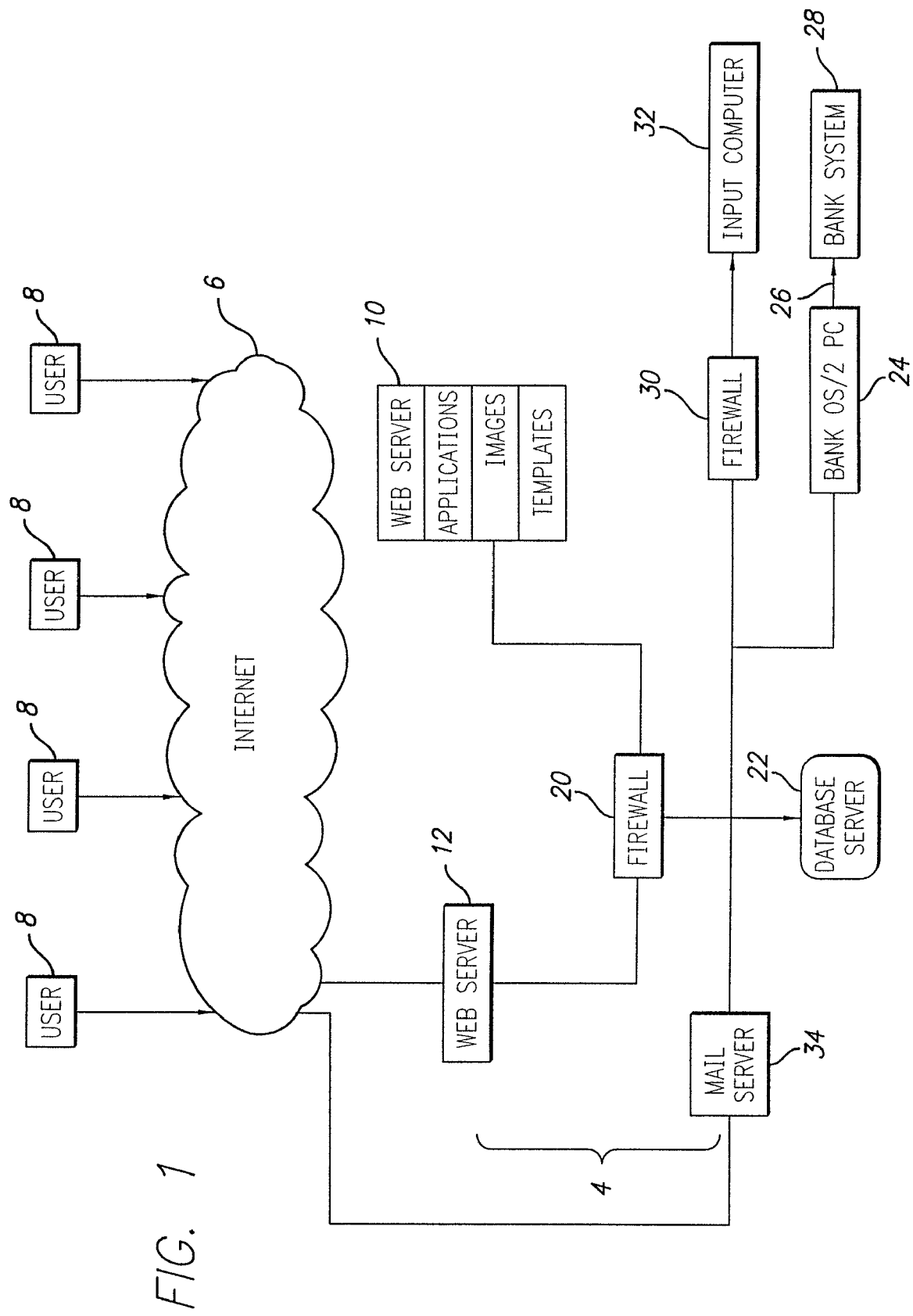
FIG. 1 is an overall view of a web-based system to provide access to a database management system of an animal genetic database and a health assessment database of the disclosure, in relation to the Internet.

The present disclosure will now be described in detail with reference to a few preferred embodiments thereof, as illustrated in the accompanying drawings. In the following description, numerous specific details are set forth in order to provide a thorough understanding of the present disclosure. It will be apparent, however, to one skilled in the art, that the present disclosure may be practiced without some or all of these specific details. In other instances, well known process steps have not been described in detail in order to not unnecessarily obscure the present disclosure.

General

There is provided a method and system of obtaining and electronically delivering a diagnosis of the health of an animal through a combination of computerized data and human interpretation related to the animal. Firstly data relating to the physical characteristics of the animal is obtained. The data is obtained from at least one of a physical inspection of the animal, and family and breed history, or other analysis of the animal. The data is submitted to a clinical pathologist. A blood sample or other bodily fluid sample is obtained from the animal. The sample is submitted for laboratory analysis. A computer generated report of the laboratory analysis is obtained. The report is related to a selected supplemental database for supplemental analysis. The supplemental analysis is related to the data relating to the physical characteristics, and family and breed history. A diagnosis of the animal health is possible. There is then generated a supplemental report to support the diagnosis.

The system provides for a computerized network wherein the laboratory samples are analyzed at a first level and been reported electronically to remote clients Superimposed on that first level of reporting there is ability to obtain by computerized electronic means to provide the supplemental analysis. This supplemental analysis can be reported automatically to remotely located clients to a computerized or electronic network. The supplemental analysis can be provided by preprogrammed criteria provided by different experts in the field associated with the nature of the anticipated illness or anticipated disease.

In a selected cases wherein the supplemental analysis does not fit pre-selected criteria affecting the disease pattern and the subject animal, the report would be directed for manual interpretation by a selected expert in the field. This manual interpretation can be added to the supplemental report by keyboard input or other voice recognition software input so that a comprehensive enhanced report can be obtained. This manual interpretation will provide an enhanced report which is then communicated electronically to a remotely located client.

Diagnostic Testing

The development of one or more assays or techniques for performing the invented testing protocols, standards and procedures of the present disclosure is straightforward, and within the knowledge of a person skilled in the art. One or more of a panel of tests relate to at least one of endocrine function, immunologic function, gastrointestinal function and nutritional analysis, inborn errors of metabolism, paternity, DNA fingerprinting, hemostasis and coagulation function, vaccinal antibody status, adverse and potential adverse vaccine reaction, infectious diseases, pathology, blood typing and bone marrow analysis, cell cytotoxicity, cytokines and allergy testing, and markers of neoplastic or paraneoplastic change. These data are relevant to the likely morbidity, likely longevity, and/or the potential risk for disease or disorder for the animal.

The following are some examples of diseases, disorders, and physiologic states that use one or more of the diagnostic test panels set out below:

EXAMPLES

Example 1

Temperament and Longevity

Characteristics related to the temperament of the animal which impacts on its longevity are determined. Biological laboratory test data from a bodily fluid or tissue of an animal are analyzed. Such test data relate to the level of neurotransmitter activity of the animal. The data relate to at least one of the value of serotonin, the gamma-aminobutyric acid (GABA), the glutamate, the dopamine, the glycine, the aspartate, the acetylcholine, the norepinephrine, the histamine, the substance P, the vasopressin, the vasoactive intestinal peptide, the neurotensin, or the other neuropeptides of the animal. The value should fall within predetermined levels as a predictive determinant of the animal's temperament (passivity, assertiveness, or aggressivity).

Methods for measuring neurotransmitters are well known in the art. Neurotransmitters such as serotonin, epinephrine, norepinephrine, glutamate, and GABA can be measured by standard immunochemical techniques involving commercially available antibodies, either polyclonal or monoclonal. Such antibodies are commercially available from sources such as Sigma Chemical Company (St. Louis, Mo.). These immunochemical techniques can involve either radioimmunoassay or other well-established assay techniques, such as ELISA (enzyme-linked immunosorbent assay). These neurotransmitters can also be measured by standard non-immunochemical techniques such as gas chromatography. Neuropeptide neurotransmitters are preferably measured by immunochemical techniques.

Test panels Nos. 1, 2, 3, 8 and 10 set out below can be used to obtain data for this Example 1.

Example 2

Immune Stimulation and Cellular Inflammatory Response

Characteristics related to at least one of the immune stimulation reaction, evidence of neoplastic or paraneoplastic change, or the cellular inflammatory response of the animal are determined. Biological laboratory test data from a bodily fluid or tissue of an animal are analyzed. The test data relates to at least one of cell cytotoxicity markers, cytokine and chemokine levels, immunoglobulin levels, type and amount of lymphocyte subsets and lymphocyte markers, and markers of neoplastic or paraneoplastic change of the animal. The value should fall within predetermined levels as a determinant of the immune stimulation reaction, neoplastic or paraneoplastic change, or the cellular inflammatory response.

Methods for measuring lymphokines and other cytokines are well known in the art. These compounds are typically measured by immunochemical techniques using commercially available monoclonal antibodies or other methods.

Test panels Nos. 1, 3, 4, 8, 9 and 10 set out below can be used to obtain data for this Example 2.

Example 3

Inherited Organ Dysfunction or Dysplasia

Characteristics related to inherited organ dysfunction or dysplasia of the animal, at least one of which is neuronal, neuromuscular or renal are determined. Biological laboratory test data from a bodily fluid or tissue of an animal are analyzed. The test data relate to an amino acid, carbohydrate, lipid or other metabolic component, body fluid or tissue marker of the animal. The data includes obtaining data related to at least one of the value of the methyl malonic acid, the fucose-containing cell metabolites, blood or urine urate or uric acid metabolites, normoglycemic glycosuria, mannosidase containing cell metabolites, amino acid uria, amyloid deposition in tissues, neuronal ceroid lipofuscin deposition, and deposition of gangliosides and other lysomal storage substrates of the animal. The value should fall within predetermined levels as a determinant of the inherited organ dysfunction or dysplasia.

Test panels Nos. 1, 3, 5, 9 and 10 set out below can be used to obtain data for this Example 3.

Example 4

Autoimmune Thyroiditis

Characteristics related to autoimmune thyroiditis of the animal are determined. Biological laboratory test data from a bodily fluid or tissue of an animal are analyzed. The test data relate to a genetic marker for autoimmune thyroiditis of the animal. The data relates to at least one of the results of a comprehensive thyroid antibody test profile, DNA fingerprint (the gene map), and markers for immunoglobulin receptors on B-cells, T-cell receptors, and protein products of the major histocompatibility complex (MHC) genes (Class I and II allellic HLA, DLA or equivalent antigenic specificities of the animal. Test assays to screen for MHC genes include restriction fragment length polymorphism (RFLP), polymerase chain reaction (PCR) RFLP, PCR sequence-specific oligonucleotides (SSO) and PCR sequence-specific primers (SSP). The value(s) should fall within predetermined levels as a determinant of autoimmune thyroiditis.

Test panels Nos. 1, 2, 3 and 10 set out below can be used to obtain data for this Example 4.

Example 5

Mammary Cancer

Characteristics related to presence of or susceptibilty to mammary cancer of the animal are determined. Biological laboratory test data from a bodily fluid or tissue of an animal are analyzed. The test data relate to estrogen (estradiol-17β), estrogen receptors, interleukin (IL) 6, progesterone, and progesterone receptors. The value should fall within predetermined levels as a determinant of the presence of or susceptibilty to mammary cancer.

Test panels Nos. 1, 2, 3 and 10 set out below can be used to obtain data for this Example 5.

Example 6

Immune Surveillance

Characteristics related to the tissue environment of the eye and brain (ocular and blood-brain barrier) which are sites protected from the normal immunologic surveillance mechanisms are determined. Biological laboratory test data from a bodily fluid or tissue of an animal are analyzed. The test data relate to the soluble and cellular immune inflammatory response mediators (cytokine and chemokine levels, immunoglobulin levels, and lymphycyte susbset markers). The value should fall within predetermined levels as a determinant of integrity of protected immune surveillance mechanisms.

Test panels Nos. 1, 3, 5, 6, 8, 9 and 10 set out below can be used to obtain data for this Example 6.

Example 7

Inherited Bleeding Disorders

Characteristics related to the tendency to bleed excessively are determined. Biological laboratory test data from a bodily fluid or tissue of an animal are analyzed. The test data relate to a comprehensive assessment of the hemostatic and coagulation function. The value should fall within predetermined levels as a determinant of the presence of bleeding disorder.

Test panels Nos. 1, 7, and 9 set out below can be used to obtain data for this Example 7.

Test Panels

The following are some specific diagnostic test panels and specialized diagnostic tests and test groups used to monitor health, morbidity, mortality and longevity of animals and animal families, and to predict the potential risks of disease or disorder:

Test 1: Comprehensive Diagnostic Test Panel

Patient phenotypic descriptors and genotypic descriptors/background; complete blood count (CBC) and platelet count, platelet size, platelet morphology; serum chemistry profile [e.g., AST (SGOT), ALT (SGOT), bilirubin (total, direct and indirect), alkaline phosphatase, GGT (GGTP), total protein, albumin, globulin, A/G ratio, cholesterol, BUN, creatinine, BUN/creatinine ratio, phosphorus, calcium, corrected calcium, calcium/phosphorus ratio, glucose, amylase, lipase, sodium, potassium, Na/K ratio, chloride, CPK, triglyceride, osmolality]; complete thyroid profile (total T4, total T3, free T4 (ED or other), free T3, T3 autoantibody, T4 autoantibody, TSH, thyroglobulin autoantibody); and urinalysis, urine culture, and sensitivity, if indicated.

Test 2: Diagnostic Test Panels for Endocrine Function

Patient phenotypic descriptors and genotypic descriptors/background, plus any or all of selected tests from the following list:

1) Thyroid Function: total T4, total T3, free T4 (ED or other), free T3, T3 autoantibody, T4 autoantibody and thyroglobulin autoantibody. Endogenous TSH also can be measured. Molecular screening for autoimmune thyroiditis including immunoglobulin receptors on B-cells, T-cell receptors, and major histocompatibilty complex (MHC) genes Class I and II allellic HLA, DLA, or equivalent animal antigenic specificities (RFLP, PCR/SSO, PCR/SSP).

2) Adrenal Function: cortisol (basal and after stimulation with ACTH, or serially after suppression with high or low-dose dexamethazone); endogenous cortisol; and endogenous ACTH.

3) Reproductive Function: testosterone; estradiol-17β; relaxin (pregnancy diagnosis); progesterone; luteinizing hormone; estrone sulfate; follicle stimulating hormone; vaginal cytology and/or culture; testicular cytology or biopsy; prostatic cytology, biopsy or wash; screens for ovarian or testicular remnants.

4) Pancreatic Function: amylase; lipase; glucose; glucagon, trypsin-like immunoreactivity (TLI); insulin, fructosamine; glycosylated hemoglobin.

5) Parathyroid Hormone Function: parathormone; ionized calcium.

6) Other Endocrine Function: aldosterone; 21 adrenal hydroxylase; vanylla mandelic acid (VMA, for epinephrine and norepinephrine metabolities).

Test 3: Diagnostic Test Panels for Immunologic Function

Patient phenotypic descriptors and genotypic descriptors/background, plus any or all of selected tests from the following list:

Antinuclear antibody (ANA)—if positive, run double stranded, single stranded, speckled, anti-RNA levels; Coombs' testing (direct and indirect; elution or microbeads gel-test); rheumatoid factor; serum electrophoresis—if abnormal, run immunoelectrophoresis, isoelectric focusing, immunoblotting (Western, Northern, Southern blots); immunoglobulin levels (IgG, IgA, IgM, IgD and IgE); complement levels (C1, C1a, C1 esterase inhibitor, C3, C4, C5-C9); LE-prep testing; lupus anticoagulant (dilute Russell's viper venom test or dilutional inhibitor test); urine protein SDS-gel electrophoresis; fibronectin and anti-fibronectin antibody; flow cytometry with fluorescence activated cell sorter (FACS, for leukocyte subsets and markers such as CD4+ and CD8+; leukocyte chemotaxis (leukocyte migration inhibition test, leukotrienes); cytokines including lymphokines and monokines (macrophage-derived) such as the interleukins (IL) [e.g. IL-6 regulated by estradiol-17β, IL-8 acts as neutrophil chemotactic factor], interferons, tumor necrosis factor(s), leukotrienes, colony stimulating factors, transforming growth factor-beta and chemokines (inflammatory cytokines); anti-platelet antibody tests (serum, bone marrow); anti-megakaryocyte antibody tests (IFA, elution); and anti-leukocyte antibody tests (direct and indirect anti-neutrophil cytoplasmic antibody, antilymphocyte antibody, etc.).

Test 4: Diagnostic Test Panels for Gastrointestinal Function and Nutritional Analysis Patient phenotypic descriptors and genotypic descriptors/background, plus nutritional and food supplement past and current use, plus any or all of selected tests from the following list:

Serum nutrients and vitamin analysis; CBC as in Test 1; serum chemistry as in Test 1 plus magnesium and iron; urinalysis, urine culture and sensitivity, if indicated; urine fractional excretion; serum and urine amino acid analyses; serum cobalamin (vitamin B12) and folate analysis; TLI [same as Test 2, 4)]; fecal flotation; Giardia screen, Clostridium perfringens enterotoxin test; cryptosporidiosis test (FA); toxoplasmosis test; bile acids test (resting and post-prandial); fecal alpha-1 protease inhibitor activity. If any abnormalities are present, further investigation includes ion-coupled plasma emission spectroscopy (ICP) for mineral analysis, and electrophoresis.

Test 5: Diagnostic Test Panels for Inborn Errors of Metabolism

Characteristics related to presence of or susceptibilty to mammary cancer of the animal are determined. Biological laboratory test data from a bodily fluid or tissue of an animal are analyzed. The test data relate to estrogen (estradiol-17β), estrogen receptors, interleukin (IL) 6, progesterone, and progesterone receptors. The value should fall within predetermined levels as a determinant of presence or susceptibilty to mammary cancer.

Patient phenotypic descriptors and genotypic descriptors/background, plus any or all selected tests from the following list:

Genetic screening tests including blood and urine analyses for mucopolysaccharides, cerebrosides, glycogen-storage diseases, phenylketones, phosphofructokinase, mannosidases, combined and specific immunoglobulin deficiencies/dysfunctions; skin and tissue biopsies; karyotyping for genotype determination; and DNA marker analyses.

Test 6: Diagnostic Test Panels for Paternity Testing and DNA Fingerprinting

Patient phenotypic descriptors and genotypic descriptors/background, plus any or all selected tests from the following list:

Major histocompatibilty complex (MHC) Class I and II alleles [analyses of HLA, DLA, or equivalent animal antigenic specificities]; genotyping; gene mapping and fingerprinting.

Test 7: Diagnostic Test Panels for Hemostatic and Coagulation Function

Patient phenotypic descriptors and genotypic descriptors/background, plus any or all selected tests from the following list:

Platelet count, platelet size (blood slide, mean platelet volume), platelet morphology (light, scanning, and electron microscopy); prothrombin time; partial thromboplastin time; fibrinogen; fibrin-fibrinogen degradation products (D-dimer test); platelet function tests (aggregation, release, clot retraction, whole blood aggregation, ristocetin cofactor); von Willebrand factor antigen and multimer analysis; specific coagulation factor analyses (factors II, V, VII, VIII:C, IX, X, XI, XII, XIII); fibrinolytic tests (plasminogen, plasmin, antiplasmin, tissue plasminogen activator, dilute whole blood lysis test, euglobulin lysis test); anti-thrombin III test; circulating anticoagulant tests; platelet factors 3 and 4 (heparin cofactor); protein C; protein S; kinin-kinogen tests; prekallikrein test; alpha1-antitrypsin assay; alpha2-macroglobulin assay; C1 esterase inactivator assay; anti-platelet antibody, and anti-megakaryocyte antibody tests (see Test 3).

Test 8: Diagnostic Test Panels for Vaccinal Antibody Status, and Adverse Vaccine or Potential Adverse Vaccine Reaction Patient phenotypic descriptors and genotypic descriptors/background, plus any or all selected tests from the following list:

1) Serology for Vaccinal Antibody: canine distemper, canine parvovirus, canine coronavirus, canine parainfluenza virus, infectious canine hepatitis virus, canine bordetella, canine Lyme (borrelia), canine leptospirosis, rabies virus, feline panleukopenia virus, feline leukemia virus, feline infectious peritonitis virus, feline immunodeficiency virus, feline calicivirus, feline herpesvirus, and equine herpes viruses (I-IV), etc.

2) Adverse Vaccine Reaction: Same as Test 3, but especially CBC; ANA; Coombs' test; platelet count, size, and morphology; anti-neutrophil cytoplasmic antibody, marker for vasculitis; complement tests; leukocyte chemotaxis tests; urine protein/creatinine ratio; anti-platelet antibody; immunoglobulin levels, especially IgG, IgA, IgM; flow cytometry (FACS) leukocyte subsets; cell cytotoxicity analysis; cytokines, especially chemokines; and complete thyroid autoantibody panel.

3) Potential (High Risk) Vaccine Reaction: especially for breeds such as the Akita, Weimaraner, Standard poodle, Eskimo Dog, harlequin Great Dane; CBC; ANA; platelet count, size and morphology; complete thyroid autoantibody panel; cell cytotoxicity analysis; cytokines; and immunoglobulin levels, especially IgG, IgA, IgM;

Test 9: Diagnostic Test Panels for Infectious Diseases

Patient phenotypic descriptors and genotypic descriptors/background, plus any or all selected tests from the following list:

1) North America: *Ehrlichia* species (*E. canis, E. risticii, E. equi, E. platys*, etc.); *Rickettsia rickettsei* (RMSF); *Borrelia* species (Lyme disease); *Bartonella* species (*B. henselae, B. vinsonii, B. clarridgeiae, B. kochlerae*); systemic fungal diseases (*Coccidioides* spp, *Cryptococcus* spp, *Histoplasma* spp, *Blastomyces* spp, *Aspergillus* spp, ringworm); mange mites (*Demodex, Sarcoptes, Chyletiella*, etc.); enteric diseases (*Clostridium perfringens* enterotoxin); protozoan diseases (*Toxoplasma* spp.; *Coccidia* spp; *Giardia* spp); retroviruses (feline leukemia virus, feline immunodeficiency virus, equine infectious anemia virus, bovine leukemia virus, caprine arthritis virus; Corona viruses (canine coronavirus, feline enteric coronavirus, feline infectious peritonitis virus; *Babesia* spp (*B. canis, B. gibsoni*); *Dirofilaria* spp (heartworm); other parasitic diseases (fleas, ticks, roundworms, tapeworms, hookworms, *Strongyles* and other intestinal parasites); and *Chlamydia* antigen (PCR testing).

2) International: Same as above plus *Leishmania* spp; *Trypanosoma* spp.; *Anaplasma* spp; *Yersina pestis*.

Test 10: Other Diagnostic Tests

Patient phenotypic descriptors and genotypic descriptors/background, plus any or all selected tests from the following list:

Pathology (anatomic, histological, cytologic, immunohistochemical, electromicroscopy, FACS); blood typing; bone marrow analysis and specific immunohistochemical staining; RFLP and PCR testing (applicable to many of the above categories); IFA and FA testing; ELISA testing, cell cytotoxicity testing, cytokine testing (see Test 3, other cytotoxic cell and mitochondrial tests); markers of neoplastic and paraneoplastic change (cancer); neurotransmitters including serotonin, the gamma-aminobutyric acid (GABA), the glutamate, the dopamine, the glycine, the aspartate, the acetylcholine, the norepinephrine, the histamine, the substance P, the vasopressin, the vasoactive intestinal peptide, the neurotensin, or the other neuropeptides; and amino acid profiling.

Data for Animal Health

The health care and well-being could include the nutritional management or the health management or the lifestyle management. The data base of the selected group of the species is at least one of breed, age, sex, size, weight, performance use, or geographical location.

The nutritional regimen is at least related to the nutrient or caloric composition needed for the dog subject, or the food allergies and food intolerances of the dog subject. The therapeutic intervention or maintenance needs of the dog are at least one of drugs, nutraceuticals, liquid intake, holistic treatments or exercise.

The diagnostic laboratory test data is a comprehensive general health profile and selectively at least one selected diagnostic profile for a selected subject. The laboratory data for the subject is ideally obtained over time from the same laboratory. This is likely to enhance the uniformity of the data, and render the determinations more accurate, and predictive of health, nutritional requirements, temperament, and longevity.

Enhanced health care and well-being management of the dog subject is obtained. Thus the data of the dog subject is compared to substantially or essentially current data. Similarly, by retaining a historical record of the dog subject data and relating this to the updated databases, the accuracy with which the management of the health care and well-being, and the development and design of nutritional requirements or therapeutic and maintenance interventions is significantly enhanced. In this manner, for instance the food, supplements, nutraceuticals and the like, can be modified by additions and/or subtractions of components based on the determined relationship, since these cumulative and dynamic data bases and data analytes change over time, whereby the determined relationship is significantly enhanced The computer program can include at least one of an expert system or interrelationship program or network for determining data base and data relationships. This can be a system such as a neural network, or other statistical sampling systems and networks, and is discussed in more detail.

The determination of the health care, well-being, nutritional or other therapeutic requirements and suggestions for promoting and maintaining health of the dog is reported on a communications network including the Internet. There is a payment procedure for the report which is achieved through the Internet. This is discussed in more detail.

An example of the comprehensive diagnostic testing used in this disclosure is shown by the test panels in the application labeled as "Test 1: Comprehensive Diagnostic Test Panel", and then there are selected examples for diagnostic panels that look at specific organ functions, such as endocrine function, immunological function, gastrointestinal function and nutritional analysis, and inborn errors of metabolism. A specific example could be the diagnostic test panel for thyroid function which depends upon the comprehensive diagnostic test panel and then more specific tests focused on the thyroid, including molecular-based testing and genomic mapping.

The term "group" here has many different characteristics. It could include, for example, a specific breed of canine, a specific purpose for which these canines are used, such as those who are purely companion pets in a home situation, performance animals for show conformation, for obedience, working trials, coursing trials, and for sheep herding and other herding purposes. It could also involve groups of animals depending on where they live—in a temperate climate, a warm or tropical climate, an arid desert climate, or a cold northern climate. It will include, of course, animals that live in urban and rural areas, animals that live near water, animals of various ages, intact or neutered sex, and for reproduction. In other words, the term "group" is used in a very broad sense here and can apply to any group that the user wishes to inquire of the database. Thus, the group is any selected subset of the healthy or diseased or disordered animals within the entire database.

The determination of the interrelationships between individuals or groups of individuals in the database can use any one of a number of computerized or other methods of analysis, simple or complex, including such things as neural networking or other kinds of relational technology evaluative databases.

Overall System

FIG. 1 is an overview of the web-based system to provide access to the invented database management system. With this system multiple users, for instance, remote users 8, access the web site 4 using the Internet 6. Each of the users 8 has a computer terminal with the appropriate software for accessing Internet. The users 8 may be unknown to the web server computers 10 and 12. Each user 8 is allowed to browse the web site and explore how the system functions.

There are several aspects to maintain security of information maintained in the database server 22 and a banking system 28. A firewall 20 prevents any user 8 from accessing any of the components behind the firewall 20. In this way the users 8 have access to the web server computers 10 and 12, but only have access to the database server 22 through the firewall 20. The database server 22 maintains, among other things, various database fields with respect to each of the health profiles of subjects and the genetic information of a subject and groups. The database 22 maintains the services with a designation associated to determine what health assessment data and genetic data can be browsed by the users 8. Each of the web server computers 10 and 12 allow users 8 to view subject and group categories and actual services and data products which are available from the database.

The web server computers 10 and 12 can be identical and can be duplicated as additional load or growth on the system occurs. The web server computers 10 and 12 share the responsibility for servicing the users of the site. This arrangement provides for expandability of the system by merely adding additional web server computers as necessary.

Preferably, the system includes an appropriate computer terminal 24 for interfacing with independent financial institutions which are connected on-line via the serial connection 26 to the financial institution computers 28. This allows automatic real time confirmation of the access of health profile and genetic data services and products. Once a user requires access to a product or service, the user goes through an identification or registration process and the exchange of financial information to allow for credit or debit card payment of the purchase. This is verified, confirmed and authorized by the appropriate bank system institution 28. Confirmation of the purchase or deposit of data, or a service is made by a mail server 34 which sends an E-mail to the user 8 confirming the purchase or deposit. The mail server 34 allows for mail to be received and sent out. Security of the various databases is maintained. Alert messages are generated when an unauthorized access is attempted. Verification messages, authorization messages and confirmation messages are generated as appropriate.

The database server 22 is also designed to interact with an input computer 32 operated by a CDPR. A firewall 30 serves to prevent unauthorized access to the database server 22 or to the input computer 32. The input computer 32 can input health profile data and genetic data to the database, after appropriate access and/or passwords are entered into the system. Similarly, users 8 through their own computers can use appropriate access codes and passwords to access input data to the database server 22. This is tightly controlled for security reasons. The data may only be added to an independent sub-database of the data server 22, and only after scrutiny by the CDPR operator of the database through input computer 32, will this data from users 8 be subsequently added to the main database server 22.

Figure 2:
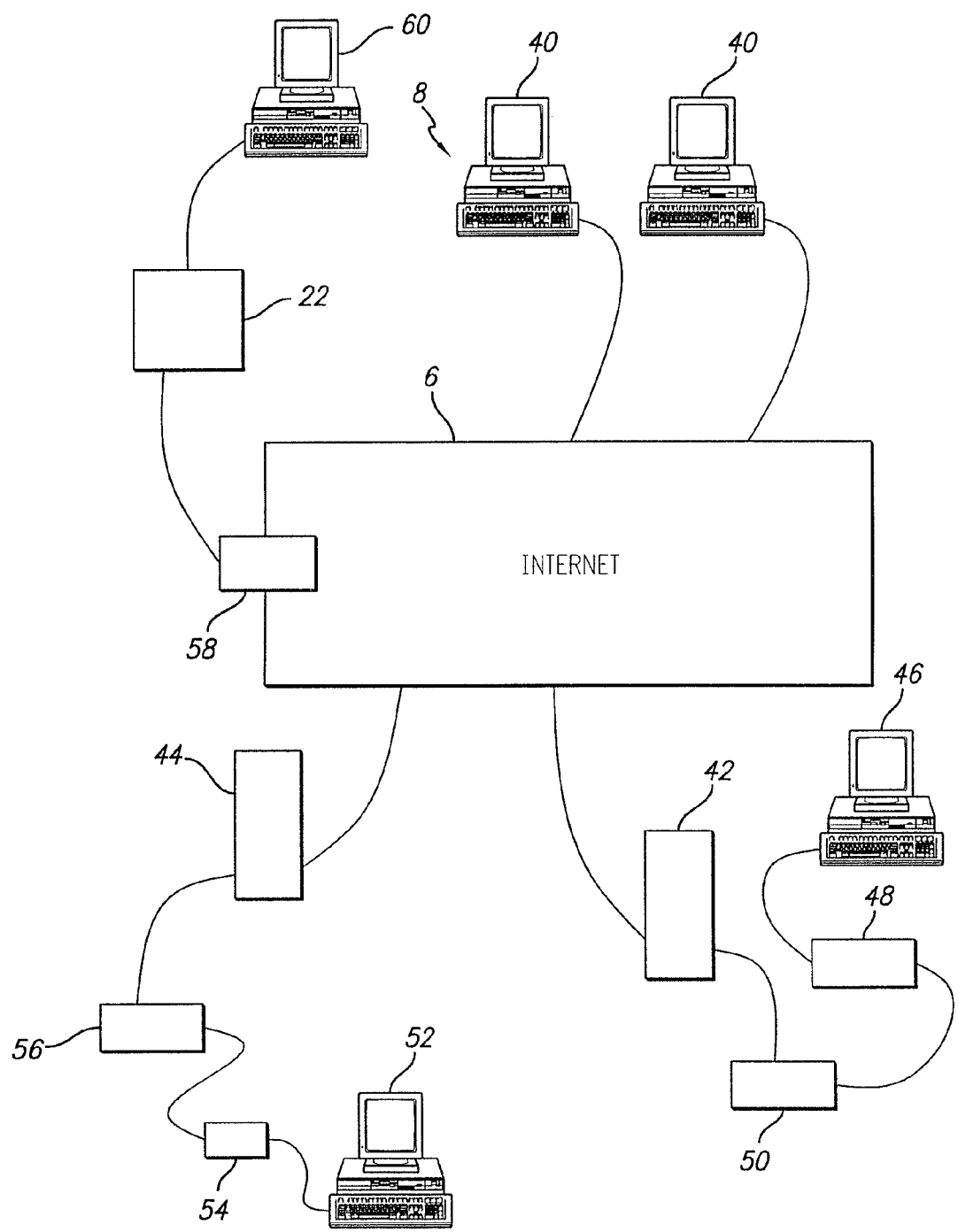
FIG. 2 is a graphical illustration of a computer network, namely the Internet.

FIG. 2 is an illustration of the Internet and its use in the system of the disclosure. The Internet 6 is a network of millions of interconnected computers 40 including systems owned by Internet providers 42 and information systems 44 such as America Online™. Individual or corporate users may establish connections to the Internet in several ways. A user on a home PC 46 may purchase an account through the Internet provider 42. Using a modem 48, the PC user can dial up the Internet provider to connect to a high speed modem 50 which, in turn, provides a full service connection to the Internet. A user 52 may also make a somewhat limited connection to the Internet through a system 20 that provides an Internet gateway connection 54 and 56 to its customers. The database 22 is also connected into the Internet 6 through an appropriate modem or high speed or direct interface 58. The database 22 is operable and maintained by the CDPR operator computer 60. Users of the databases of the disclosure would access the Internet in an appropriately selected manner.

Figure 3:
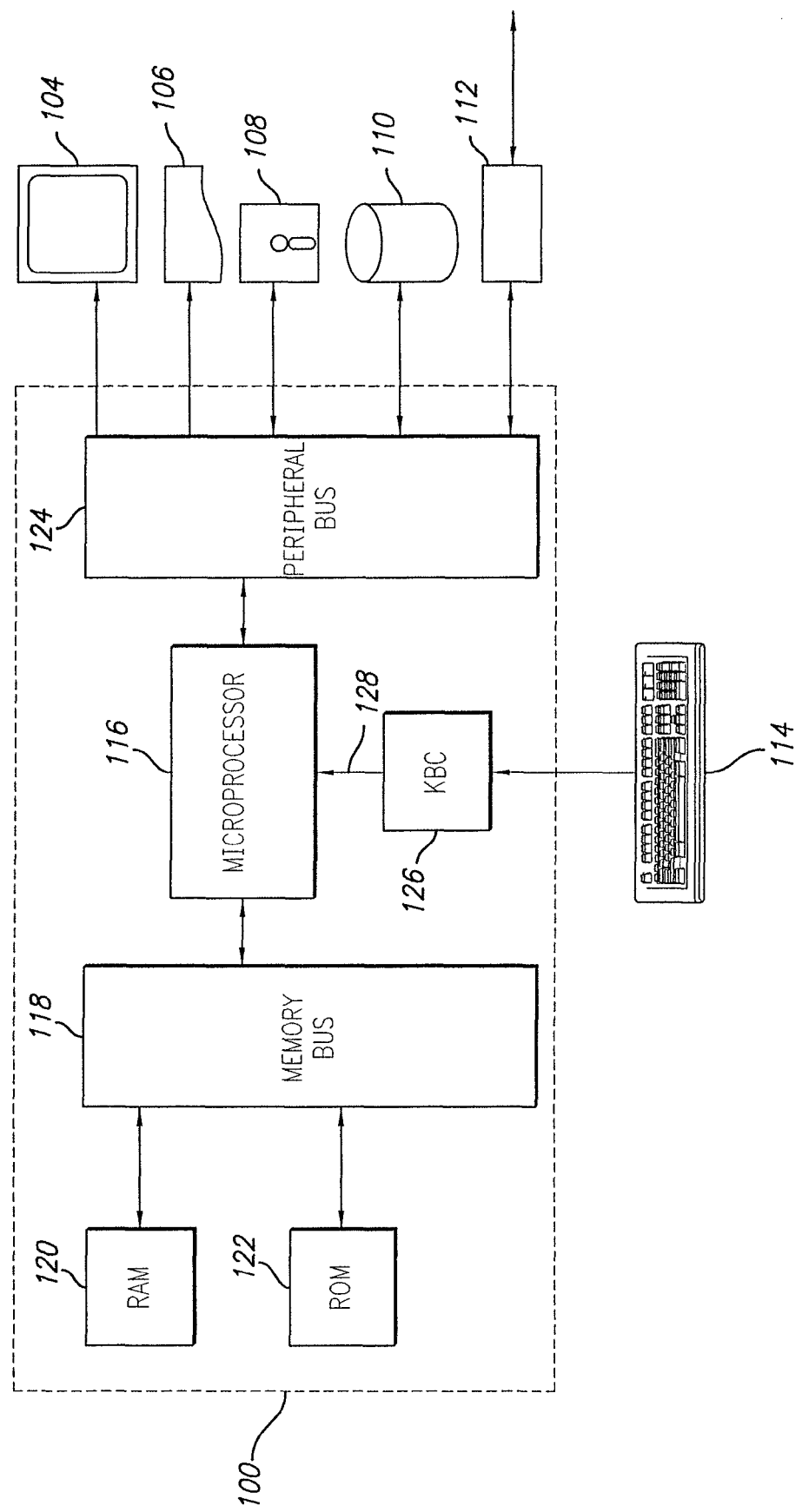
FIG. 3 is a block diagram of an exemplary computer system for practicing various aspects of the disclosure.

FIG. 3 is a block diagram of an exemplary computer system 100 for practicing various aspects of the disclosure. The computer system 100 includes a display screen or monitor 104, a printer 106, a disk drive 108, a hard disk drive 110, a network interface 112, and a keyboard 114. The computer system 100 includes a microprocessor 116, a memory bus 118, random access memory (RAM) 129, read only memory (ROM) 122, a peripheral bus 124, and a keyboard controller 126. The computer system 100 can be a personal computer, such as an Apple computer, e.g., an Apple Macintosh™, an IBM™ personal computer, or a compatible, a workstation computer, such as a Sun Microsystems™ or Hewlett-Packard™ workstation, or some other type of computer.

Microprocessor 116 is a general purpose digital processor which controls the operation of computer system 100. Microprocessor 116 can be a single-chip processor or can be implemented with multiple components. Using instructions retrieve from memory, the microprocessor 116 controls the reception and manipulation of input data and the output and display of data on output devices.

Memory bus 188 is used by the microprocessor 116 to access RAM 120 and ROM 122. RAM 129 is used by microprocessor 116 as a general storage area and as scratch-pad memory, and can also be used to store input data and processed data. ROM 122 can be used to store instructions or program code followed by microprocessor 116 as well as other data.

Peripheral bus 124 is used to access the input, output, and storage devices used by computer system 10. These devices include the display screen 104, printer device 106, disk drive 108, hard disk drive 110, and network interface 112. The keyboard controller 126 is used to receive input from the keyboard 114 and send decoded symbols for each pressed key to microprocessor 116 over bus 128.

The display screen or monitor 104 is an output device that displays images of data provided by microprocessor 116 via peripheral bus 124 or provided by other components in computer system 100. The printer device 106 when operating as a printer provides an image on a sheet of paper or a similar surface. Other output devices such as a plotter, typesetter, etc. can be used in place of, or in addition to the printer device 106.

The disk drive 108 and hard disk drive 110 can be used to store various types of data. The disk drive 108 facilitates transporting such data to other computer systems, and hard disk drive 110 permits fast access to large amounts of stored data.

Microprocessor 116 together with an operating system operate to execute computer code and produce and use data. The computer code and data may reside on RAM 120, ROM 122, or hard disk drive 120. The computer code and data could also reside on a removable program medium and loaded or installed onto computer system 100 when needed. Removable program mediums include, for example, CD-ROM, PC-CARD, floppy disk and magnetic tape.

The network interface circuit 112 is used to send and receive data over a network connected to other computer systems. An interface card or similar device and appropriate software implemented by microprocessor 116 can be used to connect computer system 100 to an existing network and transfer data according to standard protocols. As such the computer system is connectable through an interface device with the Internet 6.

Keyboard 114 is used by a user to input commands and other instructions to computer system 100. Other types of user input devices can also be used in conjunction with the present disclosure. For example, pointing devices such as a computer mouse, a track ball, a stylus, or a tablet can be used to manipulate a pointer on a screen of a general-purpose computer.

The present disclosure in relation to the animal database management of data can also be embodied as computer readable code on a computer readable medium. The computer readable medium is any data storage device that can store data which can be thereafter read by a computer system. Examples of the computer readable medium include read-only memory, random-access memory, magnetic data storage devices such as diskettes, and optical data storage devices such as CD-ROMs. The computer readable medium can also be distributed over network coupled computer systems so that the computer readable code is stored and executed in a distributed fashion.

Specific System

Figure 4:
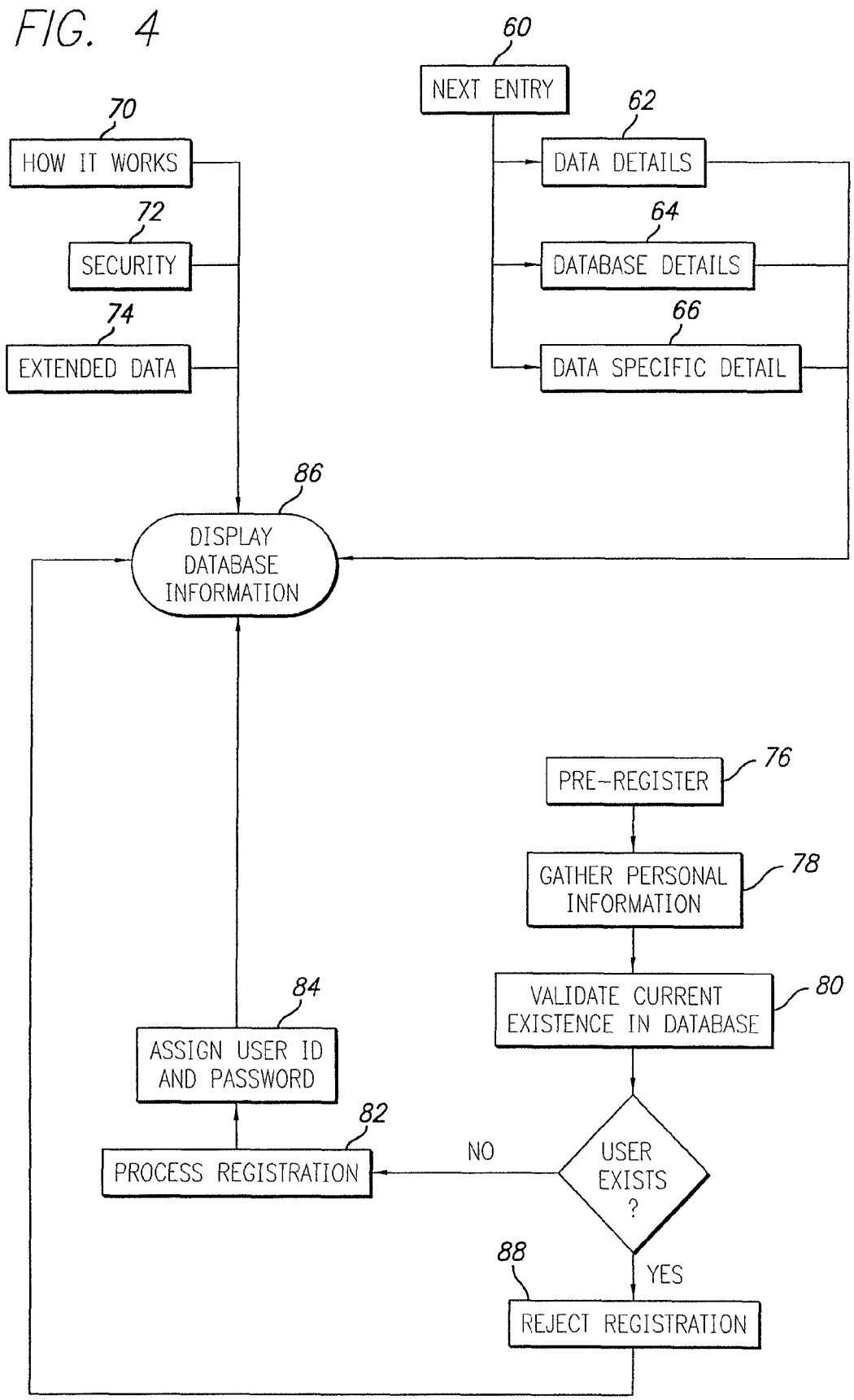
FIG. 4 is a view of a browser for the database management system for accessing an animal genetic database and a health assessment database of the disclosure.

FIG. 4 illustrates a browser system for use with the database system of the disclosure. A browser goes through a number of preliminary screens and logic steps, and reaches a screen 60 entitled "Next Entry". This screen provides data details or information generally indicated as 62. Clicking on any of these categories allows the user to review database details 64, data specific details as generally indicated by 66. In this way, the user can index through a number of screens to get information regarding the different databases of the system. In addition, clicking on any of the triggers 70, 72, 74 and 76 is possible. These correspond to HOW IT WORKS, SECURITY, EXTENDED DATA and PRE-REGISTRATION. Clicking on trigger 70 provides the user with information on how the process works, explains the system, and provides details on how the user can participate in the database and obtain data or input data. Clicking on trigger 72 provides details regarding security of the system and automatic payment. In some cases, products and services are offered with extended data and clicking on trigger 74 which can provide details of the extended data and explains that this may only be available on certain services or products.

Trigger 76 allows a user to pre-register and obtain user ID number. This ID number is combined with financial information retained in the database in an encrypted form. The pre-registration trigger 76 follows with step 78 which is to gather personal information such as credit card number and expiry date to allow for automatic payment. Step 80 is to validate a current existence in the database, if this occurs. With a negative answer, the user is directed into a registration process indicate as 82. A user ID is assigned and a password is entered. This information is maintained in a portion of the database 22. At 84 the user is provided a screen identifying the user ID at screen 86. If the user already exists, the registration process is rejected at 88 and the user is advised of the information at the display 86. The screen at 86 would also represent the information which is available in the database 22.

Figure 5:
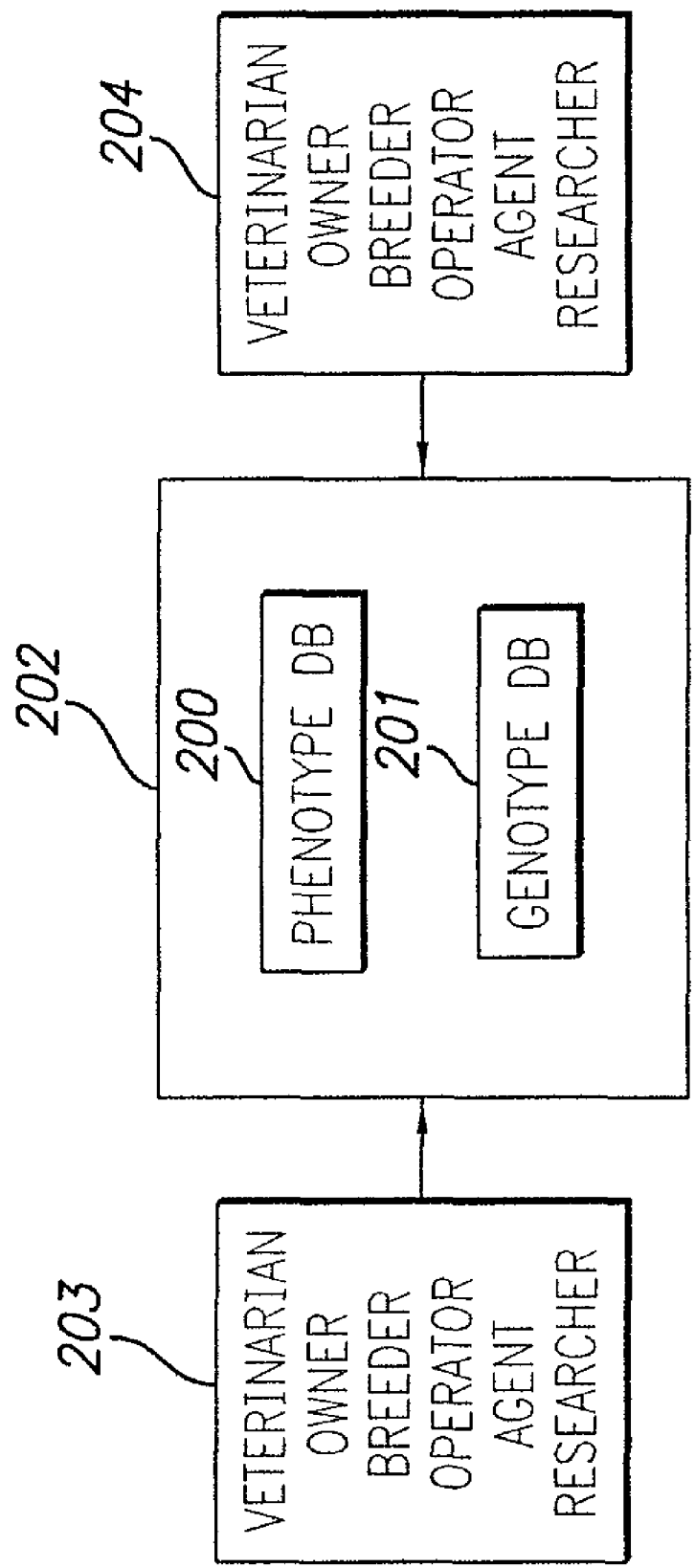
FIG. 5 is a basic flow diagram illustrating an exemplary process by which an operator of a CDPR receives and transmits data relating to health assessment and genetic information.

In FIG. 5 there is shown a basic block diagram of the components making up the CDPR. There is the phenotype database or physical health database 200 and a genotype database or genetic information database 201. These are contained in part of the overall CDPR database 202. User input 203 can be obtained from a remote user such as a veterinarian, owner, breeder, or the operator of the database, an agent or researcher. The output from the database 204 could be to the veterinarian, owner, breeder, operator, agent or researcher.

Figure 6:
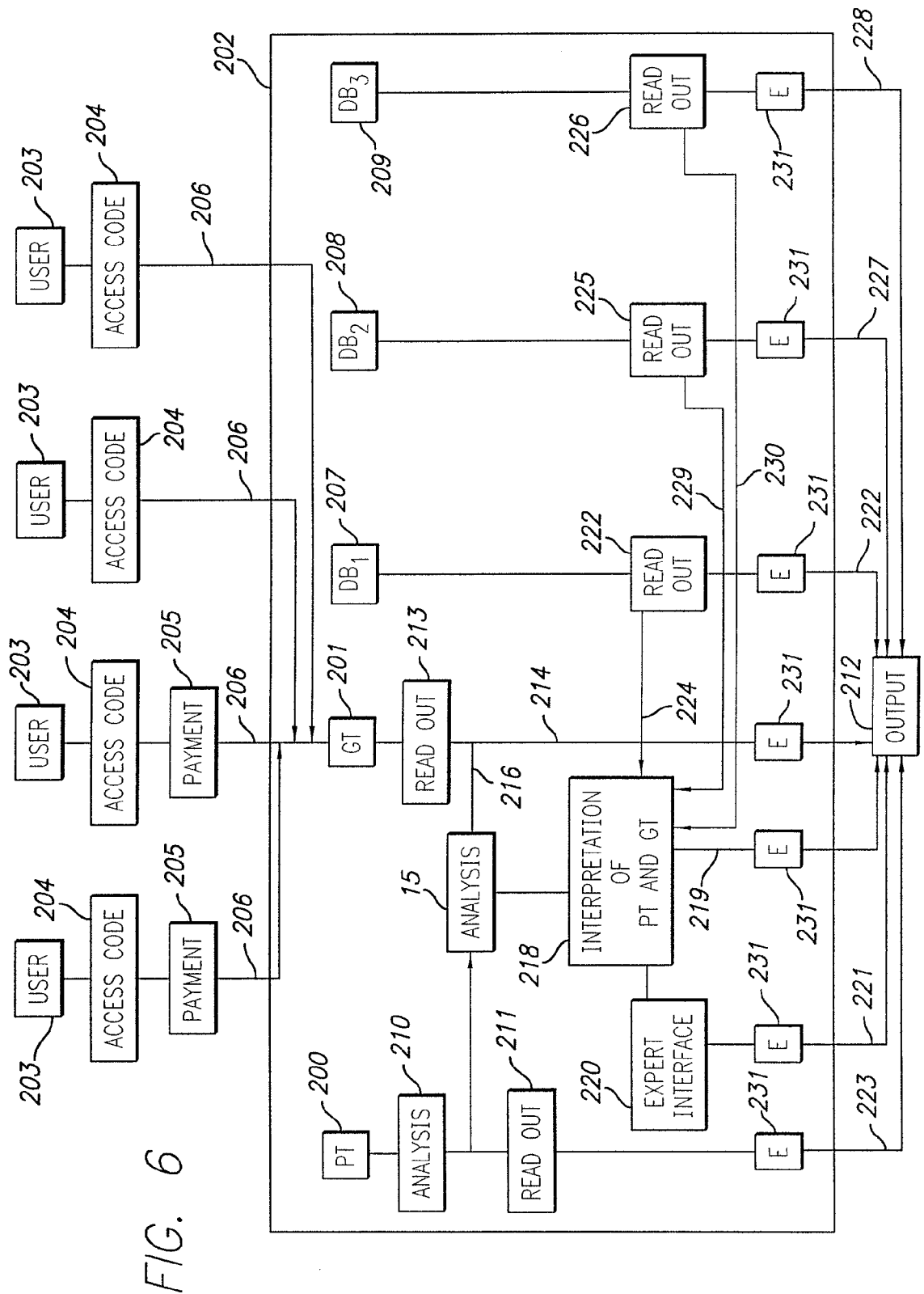
FIG. 6 is a detailed flow diagram of the system steps employed in one embodiment of the present disclosure wherein a remote user accesses and outputs data.

FIG. 6 shows a relationship for retrieving data from the database 202. The user 8 is represented here as a veterinarian, owner, breeder, operator, or researcher 203 who accesses the CDPR 202 accesses a first screen through a computer network 6 which inquires about information about the user. An access request message is sent, and an appropriate access enabling message is transmitted. The user 203 can obtain partial or full access to the CDPR 202 according to the scale of authority given to the user 203 to access data. There is a computer program system 205 to ensure that payment is made as appropriate before access to the CDPR 202 is granted. In some situations, the appropriate access code 204 can permit bypassing the payment requirement 205 as indicated by line 206. Payments 205 through the computer program can be effected by a credit card entry and automatic transfer to a financial institution on behalf of the operator of the CDPR 202. Such payment for access to the database is effected by a system which is well known in the art. The financial institution will appropriately credit the operator of the CDPR 202 in a financial manner as established between the operator and the financial institution.

Within the CDPR 201 there is the ability to access the physical health phenotype database 200, the genotype database 201, and other databases 207, 208 and 209, respectively. The phenotypic and genotypic information together with other database information can be presented on a single screen or monitor or other viewing means, for instance, hard copy format. The access therefore can be to multiple databases contained within the CDPR 202. After accessing the physical health database 200, the user obtains an analysis report from module 210. The user is then able to read the analysis as indicated by 211 and output the analysis from the read-out 211 as indicated by output 212. The output 212 can be a computer screen read-out, fax or voice information.

The physical health or phenotype database 200 is subject or group specific. In other words, the data obtained in that database is specific to a particular animal or animal group (breed, family, species, etc.) which has been the subject of a laboratory or research biological examination such that fluid or tissue samples have been subject to analysis in one or more laboratory or research environments. These biological reports can include those from specimens of blood, urine, other body fluids, skin, eyes, skeletal and other tissues. The PT database 200 has the ability to store the subject specific information as required within the CDPR 202.

The genotype specific or genetic disorder or disease data is retained in the database 201 within the CDPR database 202. This data is either subject specific, family specific, breed specific, species specific, disorder specific, or disease specific, and is group or subject specific. The user can access the genotype database 201 and obtain a read-out 213 which can then be transmitted along line 214 to an output 212 in the same manner that the physical health assessment is obtained as an output.

In an alternative approach, the reader can request an analysis 215 from the genotype database as indicated by line 216. This analysis can receive data along line 217 from the analysis information of the physical health assessment. Interpretation of the PT and GT can be obtained as indicated by 218, and this can then be outputted as indicated along line 219. The interpretation of PT and GT 218 can be performed by an algorithm relating to the coefficients and predictability of information relating to disorders, disease and longevity when considering the data from the two databases PT 200 and GT 201. This can be done automatically and outputted along line 219, or there can be an expert interface 220 using skilled personnel to interpret the data of block 218, and this can, in turn, be outputted along line 221 to the output 212.

Database 207 can be a genetic marker database, and the information from that database can be directly input into the output through a read-out 222 and 223 to the output 212. Alternatively, the data from database 207 can be added to the interpretation section 218 of the physical health and genetic information by directing the data along line 224. This data can then be made the subject of the output along the line 219 and 221 as required.

Similarly other databases 208, 209, respectively, have read-outs 225 and 226 which can be directly coupled along lines 227 and 228 to the output, or can be directed optionally along lines 229 and 230 to the interpretation module 218. It can then be the subject of interpretation for an expert interface 220 review which is, in turn, made the subject of the output 219 and 221.

In each of the output lines 219, 221, 222, 223, 227, 228, and 214 there is also provided an encryption program 231 which can be optionally used in the system. The output 212 can include paper, electronic, or voice read-out as is required.

In this manner, the output 212 provides a compilation which combines the physical health and genetic information relating to a subject, the breed, disease, disorder and lifespan, thereby enabling the receiver of the output 212 to use the compiled information in a manner to facilitate breeding criteria which can be important in relation to animals which are usually inbred or line bred. The information can also be used to facilitate on-going monitoring of particular subject animals. The data from this system can be used to manipulate and regulate breeding, health, and longevity effectively among animals.

Figure 7:
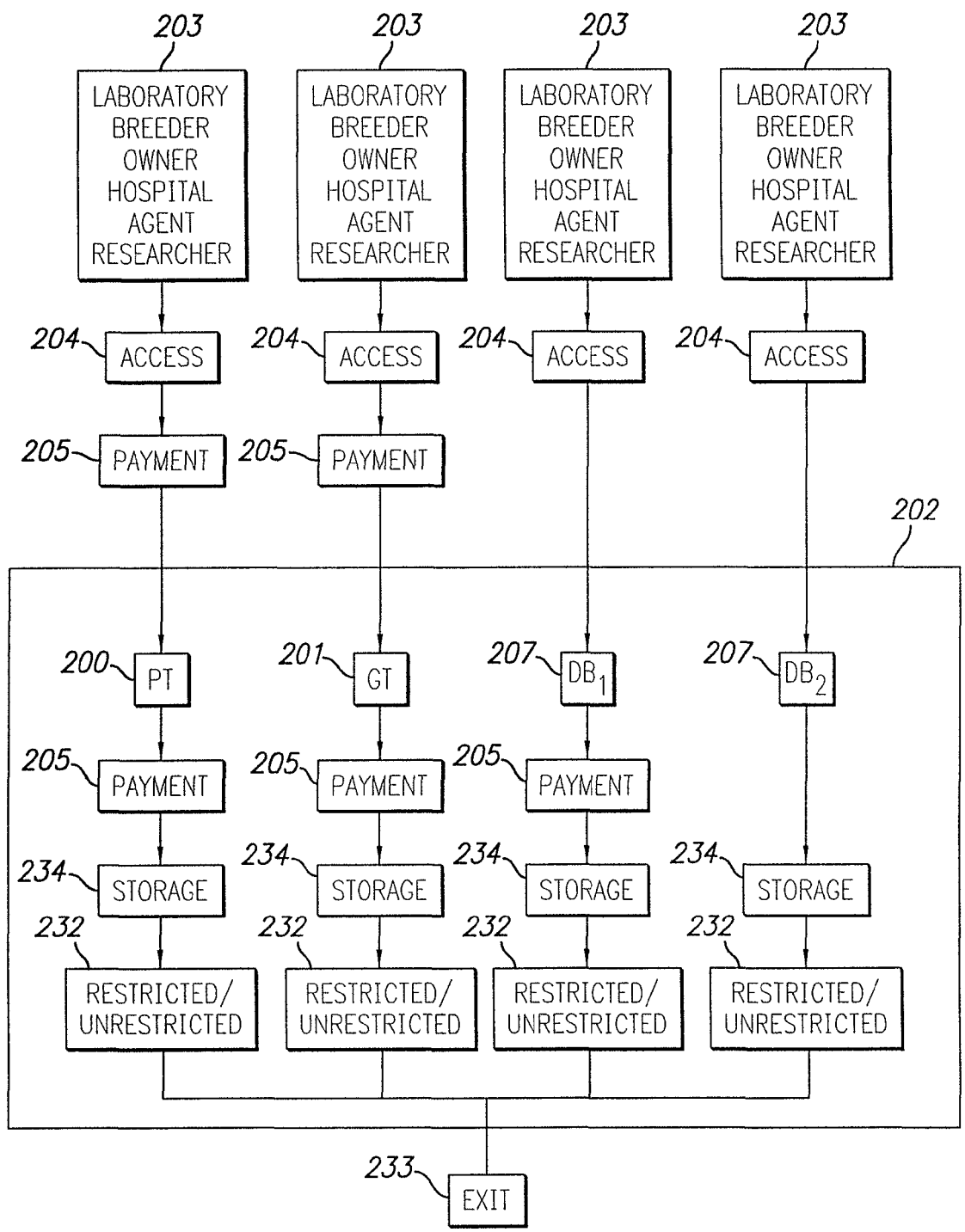
FIG. 7 is a detailed flow diagram of the methods and steps employed by a remote user to add data to the database.

The system of the disclosure is further described with regard to FIG. 7 which is a system for inputting data to the CDPR 202. Here multiple users 203, which can be a remote user such as a laboratory, a breeder, an owner, hospital, agent, or an operator of the CDPR 202 accesses the system through module 204 which, in turn, accesses the CDPR 202. Appropriate access request and access enable messages are sent. Within the CDPR 202 there is a physical health or phenotype module 200, a genetic or genotype data module 201, and other database modules 207, etc. After accessing the CDPR 202, additional data can be added to the modules 200, 201, 207, etc. through any of the users 203, if authorized. Depositing data into each of the modules 200, 201 and 207 can optionally require the payment to the operator of the CDPR 202 as is indicated by block 205. This system can function in the same manner as the retrieval of data from CDPR 202.

The stored data in each of the blocks 200, 201, and 207 can be set up as indicated by block 232 in a manner which is restricted or unrestricted to selected users 203. This may be necessary according to the protocols governing the inputted data to the different databases. In some cases, the waiving of deposit fees is made in the interest of freedom of the database to subsequent users who wish to retrieve data from the database. After storage of the data as indicated by block 234, the user 203 exits CDPR 202 as indicated by block 233.

As is apparent, the physical health or phenotype profile of subject animals is dynamic and grows as more data is added into the system. Likewise, the genetic genotype database also grows as increasing research of particular subjects, breeds, and the like is obtained. The deposit of new information into the CDPR 202 is regulated in a manner that the data cannot distort the databases 202 in an in appropriate manner. Likewise, users 203 cannot access the secured databases within CDPR 202 in an inappropriate manner.

Different algorithms regulate the relationship between the health profile, the genetic data, and other data relating to animals. These algorithms determine the probabilities, possibilities, and likelihood of disorders and disease in subject animals and offspring animals. They are used as predictors of the future evolvement of health of the animal.

Analyzing the data from the CDPR 102 in the manner of the present disclosure permits for genetic screening, health assessment profiling, and the diagnostic, prophylactic, and therapeutic management of animals.

An exemplary server performs all the operations of a conventional database system and performs additional operations in accordance with the present disclosure as has been discussed. The server includes a central processing unit (CPU) together with associated memory for processing information about different animals species and history. The inquiries concern animals species and history and inquiries and requests for health profiling and genetic information, and providing health profiles and genetic information. The CPU is coupled to the database and to users via a communications port. The CPU is also coupled to an electronic mail processor for processing and storing (in a storage device) e-mail messages transmitted between the CPU and various agents, users and the like. The CPU is further coupled to a data storage device. A data storage device may include a variety of the databases. The system permits for the requesting, storing and providing of data with respect to animal phenotypic information and genetic information. The format and content of the databases have been discussed in detail.

In one form of the disclosure, the desired data is based on the submission of test specimens of a specific animal to the laboratory. In some other cases health profile test data 200 can be inputted into the CDPR 202 having the genetic database 201. The CDPR 202 can perform an analysis and correlation between the health profile database 200 and the genetic database 201.

Using the communications link, the remote user 8 communicates with the laboratory or the CDPR 202. Specimens can be packaged and physically transported to the laboratory site via commercially available common carriers, such as the postal service or courier services. When the packages arrive, the laboratory places them in storage, or the tests are performed. Instruments 300 perform the tests to obtain data as specified by the remote user 8. The biohazardous samples can be disposed of a waste material. The test results, or output is provided as part of a health profile database 200 of the CDPR 202 and is available to the remote user 8.

If desired, the remote user 8 can arrange to have the data stored in the CDPR 202, made available to other remote users 8. The remote user 8 can also request the laboratory to perform analysis on the health profile data 200 generated.

In one embodiment, the communications link is a computer network and the message transfer modality is, for instance, the Internet 6, and/or an Intranet and/or an Extranet. The network systems are particularly suited to the application described herein since it offers global or widespread accessibility and high speed data transfer of large amounts of information.

A security unit allows remote users to designate who has permission to view or use their data. Feasible options for these information management requirements include: access by the submitting remote users only, access by certain designated researchers and collaborators, time-embargoed data followed by wider access, and unrestricted access by all. A commerce unit can implement functions related to the business aspects of the CDPR facility, including billing, inventory management of support materials.

A multimedia unit comprises means to store, manipulate, and present audio, graphical, video information. This information may include a video explaining how the CDPR is used, a visual depiction of the data, methodology, or a comment regarding the background of the data. The multimedia unit may also implement subscription functions, so that updated data automatically provided to remote users or other interested parties.

The operations performed by the present disclosure begins when the controller receives an access request message from the remote user via a communication link. Using information in the access request message and any other available information, the controller determines if the remote user is authorized to access the CDPR 202. If so, an access enabling message is transmitted from the controller to the remote user 8. The access enabling message can comprise a set of computer instructions transmitted over the Internet 6 which is downloaded into the remote user memory for execution by the remote user processor. These instructions may be enabling, that is, they may allow direct communication between the remote user 8 and the CDPR 202 with no further need for the controller. In another embodiment, the access enabling message may simply comprise a password or other enabling message which allows the remote user 8 to proceed. The remote user 8 can access or submit data to the CDPR 202 according to different protocols and regimes and security arrangements.

Figure 8:
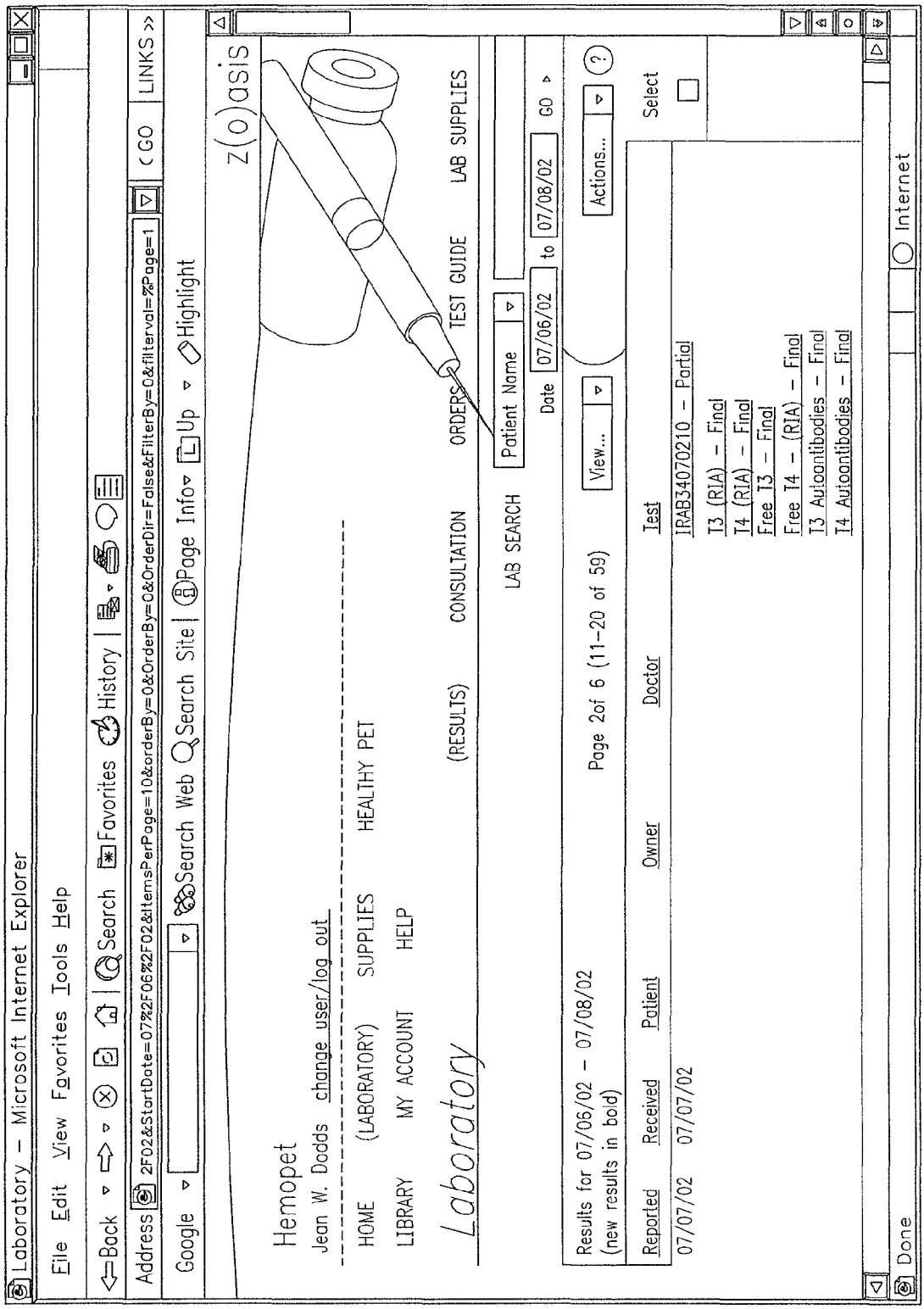
FIG. 8 is a laboratory report page from a web site showing the first level of reporting of a patient.
Figure 9:
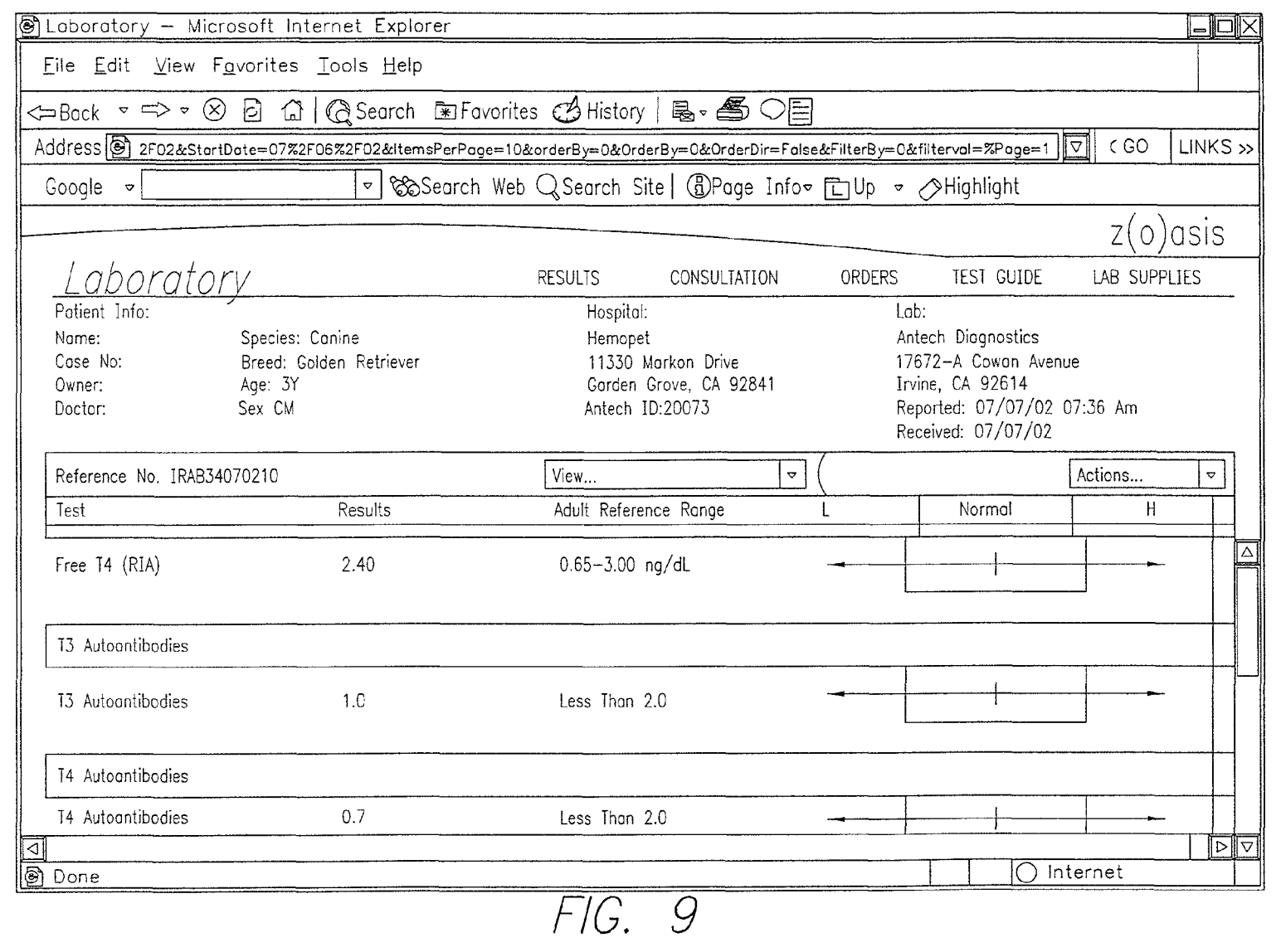
Figure 10:
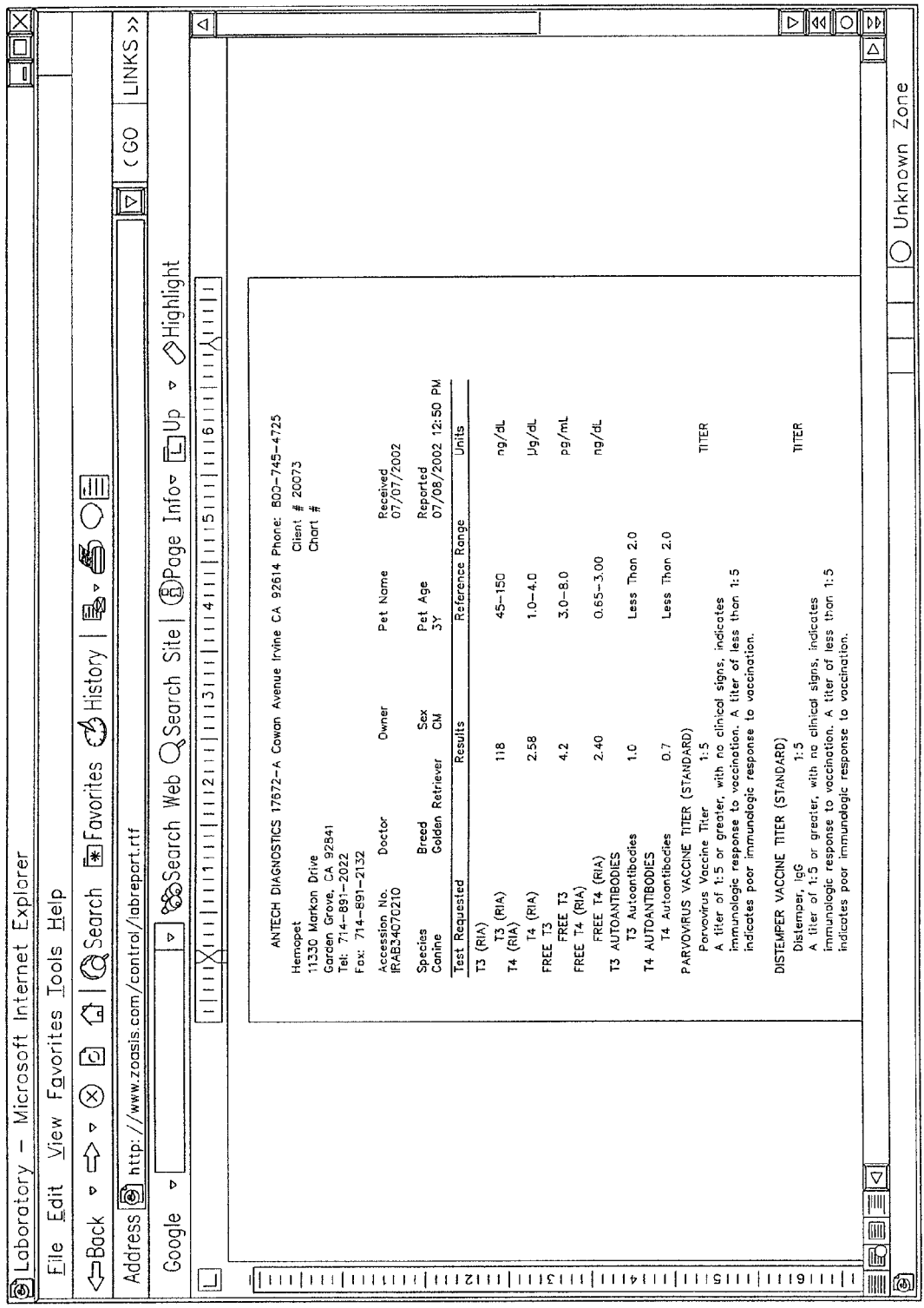
FIG. 10 is a further elaboration of the test data of FIG. 8 showing a different layout in a manner typically used for computer reporting of the test data through a web-based system.

FIG. 8 shows a typical laboratory report page from a web site showing the first level of reporting of a patient. FIG. 9 shows an expanded more detailed report of some of the test data of the patient shown in FIG. 8. A further elaboration is shown in FIG. 10. There is a different layout of the data, namely in a manner typically used for computer reporting of the test data through a web-based system. FIG. 11 shows the print out of the test data report as shown in FIG. 10.

Figure 12:
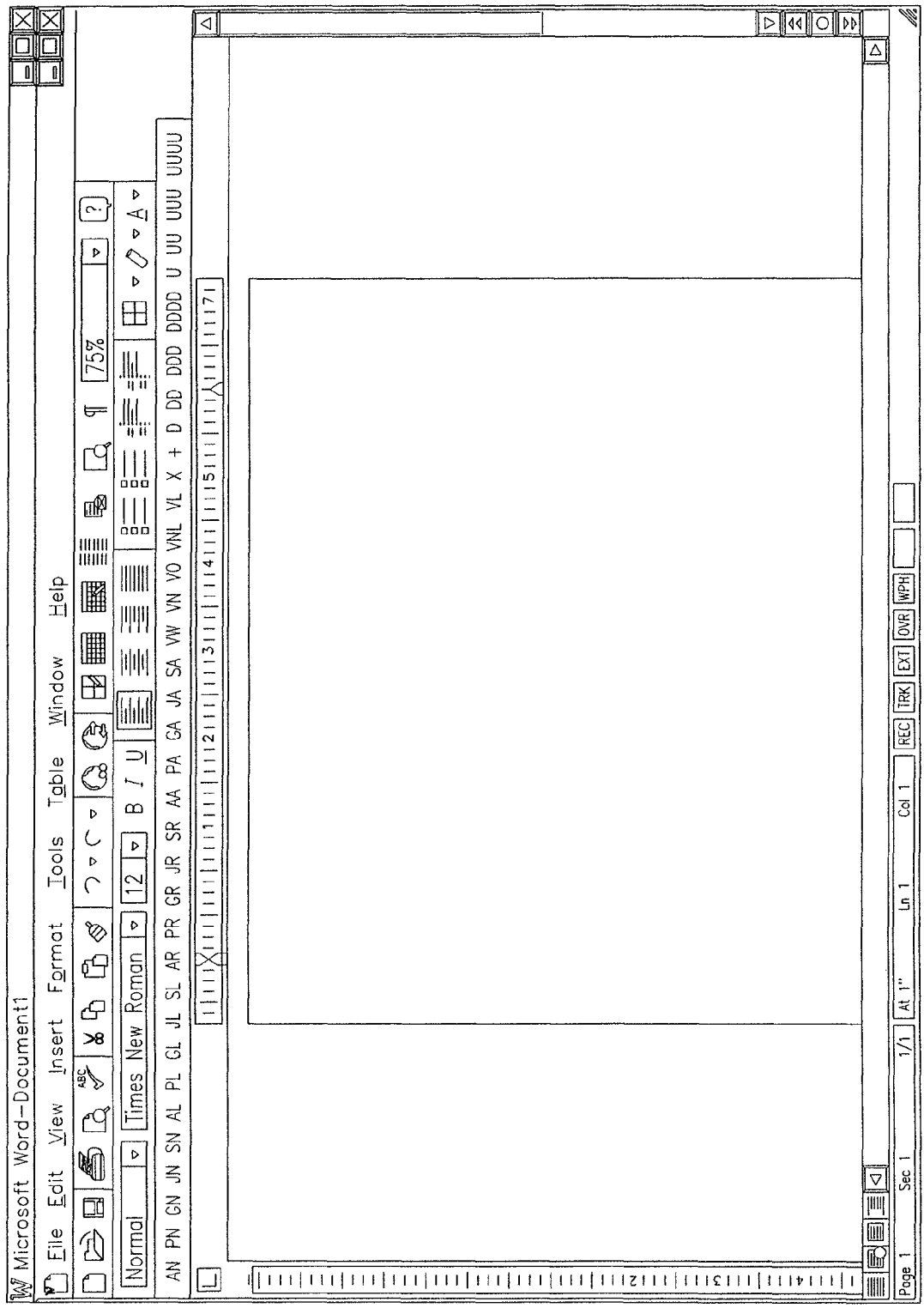
FIG. 12 is a screen view of a word processing program with a blank new page, and showing a toolbar with icons arranged to represent text relating to a diagnosis and recommendation.

FIG. 12 is a screen view of a word processing program with a blank new page, and showing a toolbar with icons arranged to represent text relating to a diagnosis and recommendation. This is part of a drop down menu. FIGS. 14A and 14B are representations of the test data report of FIG. 11 having superimposed additional data inserted through the use of selected icons on the tool bar of FIG. 12, and having added manually written comments. FIGS. 15A to 15C represent different diagnostic comments represented by the use of different icons from the toolbar A diagnosis of the health of an animal is obtained through a combination of computerized data and human interpretation. Data relates to the physical characteristics of the animal, and includes data obtained from a physical inspection of the animal. A blood or other fluid sample is used to obtain a computer generated laboratory analysis. This is reported through an internet network to the clinical pathologist. The clinical pathologist has the data relating to the physical characteristics, and thereby makes a diagnosis of the animal health. A drop-down menu on a computer screen provides supplemental reports to support the diagnosis. This can be enhanced by further input from the pathologist through keyboard entry into the computer to obtain an integrated computer report having the laboratory analysis, supplemental report, and selectively an enhanced report. The integrated report is electronically communicated to a client.

A method and system of obtaining and electronically delivering an assessment of the thyroid function of an animal is achieved through a combination of computerized data and human interpretation related to the animal. Data relating to the physical characteristics of the animal is obtained, the data being from at least one of a physical inspection of the animal, and the data submitted to a clinical pathologist. A blood or other body fluid sample from the animal is submitted for laboratory analysis of the total T4, total T3, free T4, free T3, T3 autoantibody, T4 autoantibody and thyroglobulin autoantibody.

A computer generated report of the laboratory analysis is obtained, and reported through a network, selectively an internet network, to a clinical pathologist. The clinical pathologist has the data relating to the physical characteristics, and makes a first assessment off the thyroid function of the animal. From a drop-down menu on a computer screen a supplemental report to support the assessment is generated. This can be selectively enhanced by a further input from the pathologist through data, selectively, keyboard, entry into the computer. The assessment is dependant on animal grouping and/or on animal age. This can include animal sex, performance type, size and the dependent on whether the animal is a rural or urban area. Other factors such as animal diet and exercise or activity level can also impact the thyroid assessment. An additional parameter which could be measured to assist in the thyroid assessment the thyroid stimulating hormone.

An integrated computer report having the laboratory analysis, supplemental report, and selectively an enhanced report is communicated to a remote client, such communicating being electronic.

The laboratory analytical report is reported in a first computer program and the drop down-menu is in a second computer program. The data from the first computer program is transferred to the second computer program.

The electronic communication to the client is selectively by email or fax, and wherein the second computer program includes a utility to transmit the integrated report form the second program through the utility.

The drop down menu is contained in a tool bar supplementing a word processing program. The tool bar includes icons defining predetermined supplemental report characteristics, and selected icons may be used by the clinical pathologist to supplement the laboratory analytical report. The icons can be grouped for animal characteristics dependant on age. Alternatively or additionally the icons are grouped for animal characteristics dependant on animal grouping. Alternatively or additionally the icons are grouped for selected disease states, the states being selectively thyroid disease, behavior, autoimmune disease, and cancer. The icons also can be grouped for selected levels of immunity from disease, that being the titer of immunity from the disease in the animal, and the need for vaccination of the animal against the disease.

Different forms of expert system computing and software programming can be used to determine the relationship of the data bases and data. Parallel distributed processing, and neuromorphic systems, such as neural networks can be used. They are good pattern recognition engines and robust classifiers, with the ability to generalize in making decisions about imprecise input data. There are multitudes of different types of networks such as a multilayer perceptron which is generally trained with the backpropagation of error algorithm, learning vector quantization, radial basis function, Hopfield, and Kohonen. Some are feedforward while others are recurrent (i.e., implement feedback) depending on how data is processed through the network. Some may require training while others are unsupervised or self-organizing. This can be implemented in software or in specialized hardware.

Alternatively or additionally fuzzy logic can be used due to the dynamic nature of the data applications, rules and functions. Such logic is adaptive to the changing environment. This logic and the neural networks can be integrated in the system.

Adaptive Logic Networks technology is an effective alternative or additional technology. The Adaptive Logic Network is neurocomputing capable of modeling complex non-linear systems by using piece-wise linear data. The inputs to an Adaptive Logic Network may be the data from large databases as described, observations recorded by a scientist, veterinarian or owner. The outputs of an Adaptive Logic Network can be used for analysis, prediction, or real-time management.

CONCLUSION

As is clear the tests above which relate to at least one of endocrine function, immunologic function, gastrointestinal function and nutritional analysis, metabolism, paternity, DNA fingerprinting, hemostasis and coagulation function, vaccinal antibody status, adverse vaccine reaction, infectious disease, pathology, anatomic, histological, cytologic, immunohistochemical, electromicroscopy, FACS, blood typing, bone marrow analysis and immunohistochemical staining, and allergy reaction about the animal provide useful information. This is in a manner previously not obtained.

As the above demonstrates, there is a need for providing data analysis and dissemination services to a wide variety of globally-distributed remote users. There is a need for providing a system for inputting, storing and retrieving data related to animal health assessment and genetics in a manner which permits for the effective use of this information.

The system also permits for the access to the genetic and/or phenotype data through a password and a system whereby access to the data generates a fee. This system permits for the access or to provide data with regard to credit cards or the like to ensure that the fee is transmitted automatically to a banking system for the account of the database when such data is accessed.

This system also provides for a situation wherein payments can be made by credit card for requests to perform health assessment profiles and secure genomic mapping and genetic screening information. Such bioinformatics system can also permit for the automatic payment for such services and products to the banking system of the database or laboratory. As such, the database may require that the payments be guaranteed, for instance by supplying a credit card number with a request for performance of services and a product, and for the retrieval of such data.

A user can submit a request to the database in any number of ways. For example, the request can be submitted via on-line direct connection, namely through a computer network such as the Internet. An intermediate researcher such as a veterinarian or scientist other than the owner could also submit the request on behalf of the owner using the e-mail capabilities of the central database system. Alternatively, the user can submit the data via an interactive voice response unit coupled to the database system of the supplier. In some situations, the database supplier can decide whether to supply the health assessment information and/or genomic mapping and genetic screening information based on the criteria of the user or its intermediary agent. Such user or intermediary agent can be notified of the decision via the interactive response unit or a live operator.

The user or agent can log into the database system and obtain the necessary records relating to an animal physical health and/or genetic ancestry or offspring. The database system can transmit in real time or on a periodic basis as determined, thereby, providing information regarding the health assessment or the genetic background and forward this information to the user and/or its intermediary agent.

The data storage devices of the disclosure include a variety of databases including a database relating to the phenotypic data of a particular species, a database relating to health assessment or other phenotypic data of particular animals in a particular species, and genetic characteristics of different species and different family trees relating to different species. The family trees would contain information including the origin, genomic map, and parental lines of a species and records of health and performance of a species. These databases are interrelated in an analytical manner and in accordance with different algorithms of permutations and probabilities to facilitate useful output information based on the combination of data in the genotypic and the phenotypic databases, and the selected databases.

Many other examples of the disclosure exist, each differing from others in matters of detail only. The disclosure is to be determined solely by the following claims.

What is claimed is:

1. A method of analyzing nutrition for a canine or feline animal, comprising:
   accessing at least one database that comprises first data relating genetic descriptor genomic data to a physiological condition, wherein the genetic descriptor genomic data is obtained from either a bodily fluid or tissue sample;
   accessing second data comprising the effect of nutrition on the expression of the genetic descriptor genomic data;
   analyzing, by use of a computer, the first and second data, relating the effect of nutrition on the expression of the genetic descriptor genomic data for the animal to the physiological condition, wherein the physiological condition comprises gastrointestinal function or immunological function of the animal; and formulating a nutritional diet based on the analyzed data.

2. The method of claim 1 further comprising preparing a nutritional diet based on the analyzed data.

3. The method of claim 1 wherein the animal is defined by a characteristic selected from the group consisting of one or more characteristics of breed type, specific breed, chronological age, physiological age, activity level, state of health or state of disease or disorder.

4. The method of claim 1 wherein the first data are derived from samples collected from a group of canine or feline animals representative of a range of genotypes and physiological conditions.

5. The method of claim 4 wherein the data is selected from the group consisting of breed, breed(s) of parents pedigree, sex, age, and presence or absence of hereditary conditions and disorders.

6. The method of claim 4 wherein the data is selected from the group consisting of age, weight, veterinary medical history, reproductive history, present health, disorder or disease state, activity level, temperament and presence or absence of, behavioral abnormalities.

7. The method of claim 4 wherein the first data comprises information obtained from DNA fingerprinting, PCR, restriction fragment length polymorphisms (RFLP), PCR sequence-specific primer (SSP), or PCR sequence-specific oligonucleotide (SSO) analysis.

8. The method of claim 1 wherein the first data comprises information obtained from DNA fingerprinting, PCR, restriction fragment length polymorphisms (RFLP), PCR sequence-specific primer (SSP), or PCR sequence-specific oligonucleotide (SSO) analysis.

9. The method of claim 1, wherein formulating the diet further comprises designing nutrition based on dietary modification.

10. The method of claim 4, further comprising obtaining the genotype by DNA mapping or genomic mapping.

11. The method of claim 1, wherein gastrointestinal function is assessed by serum chemistry, serum cobalamin, folate, or trypsin-like immunoreactivity (TLI).

12. The method of claim 1, wherein immunological function is assessed by serum electrophoresis, immunoglobulin levels, complement levels, urine electrophoresis, leukocyte marker levels, cytokine levels, monokine levels, or chemokine levels.

13. The method of claim 1, wherein immunological function is assessed by a saliva test for immunoglobulins IgA or IgM.

* * * * *

UNITED STATES PATENT AND TRADEMARK OFFICE
CERTIFICATE OF CORRECTION

| | | |
|---|---|---|
| PATENT NO. | : 7,865,343 B2 | Page 1 of 1 |
| APPLICATION NO. | : 12/355721 | |
| DATED | : January 4, 2011 | |
| INVENTOR(S) | : W. Jean Dodds | |

It is certified that error appears in the above-identified patent and that said Letters Patent is hereby corrected as shown below:

On the Title Page, Item 60:

The first Paragraph should read:

--(60) Division of application No. 10/635,707, filed Aug. 5, 2003, now Patent No. 7,548,839, which is a continuation-in-part of application No. 09/419,192, filed on Oct. 15, 1999, now Pat. No. 6,730,023, and a continuation-in-part of application No. 10/356,885, filed on Feb. 3, 2003, now Pat. No. 7,029,441, which is a continuation of application No. 09/898,193, filed on July 2, 2001, now Pat. No. 6,537,213, which is a continuation-in-part of application No. 09/432,851, filed on Nov. 2, 1999, now Pat. No. 6,287,254.--

In the Specification:

Column 1 lines 6 - 14 should read:

--This application is a divisional of application Ser. No. 10/635,707, filed Aug. 5, 2003, now issued U.S. Pat. No. 7,548,839, which is a continuation-in-part of and relates to application Ser. No. 09/419,192, filed Oct. 15, 1999, now issued U.S. Pat. No. 6,730,023, and also application Ser. No. 09/432,851 filed Nov. 2, 1999 now issued U.S. Pat. No. 6,287,254. This Application also relates to Provisional Application No. 60/403,203 filed Aug. 12, 2002. The contents of all those applications are incorporated by reference herein. Application Ser. No. 10/635,707, filed Aug. 5, 2003, now issued U.S. Pat. No. 7,548,839, is also a continuation-in-part application Ser. No. 10/356,885 filed on Feb. 3, 2003 now issued U.S. Pat. No. 7,029,441, which is a continuation of application Ser. No. 09/898,193 filed on July 2, 2001 now issued U.S. Pat. No. 6,537,213.--

Signed and Sealed this
Twenty-first Day of October, 2014

Michelle K. Lee
*Deputy Director of the United States Patent and Trademark Office*